(12) United States Patent
Kim et al.

(10) Patent No.: US 8,846,213 B2
(45) Date of Patent: Sep. 30, 2014

(54) ORGANIC LIGHT-EMITTING DEVICE

(75) Inventors: Young-Kook Kim, Yongin (KR); Seok-Hwan Hwang, Yongin (KR); Hye-Jin Jung, Yongin (KR); Jin-O Lim, Yongin (KR); Jong-Hyuk Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 502 days.

(21) Appl. No.: 13/181,351

(22) Filed: Jul. 12, 2011

(65) Prior Publication Data
US 2012/0012826 A1 Jan. 19, 2012

(30) Foreign Application Priority Data

Jul. 13, 2010 (KR) .................. 10-2010-0067471

(51) Int. Cl.
| | |
|---|---|
| *H01L 51/54* | (2006.01) |
| *C07D 487/00* | (2006.01) |
| *C07D 209/56* | (2006.01) |
| *H01L 51/00* | (2006.01) |
| *H01L 51/50* | (2006.01) |

(52) U.S. Cl.
CPC .......... *C07D 209/56* (2013.01); *H01L 51/5048* (2013.01); *H01L 51/0072* (2013.01); *H01L 51/0059* (2013.01); *Y10S 428/917* (2013.01)
USPC ........... 428/690; 428/917; 548/417; 313/504; 313/506

(58) Field of Classification Search
None
See application file for complete search history.

(56) References Cited

U.S. PATENT DOCUMENTS

| | | | |
|---|---|---|---|
| 2008/0124455 A1* | 5/2008 | Shin et al. | 427/66 |
| 2010/0032656 A1* | 2/2010 | Kwang et al. | 257/40 |
| 2013/0043460 A1* | 2/2013 | Cheng et al. | 257/40 |

FOREIGN PATENT DOCUMENTS

| | | | |
|---|---|---|---|
| JP | 2010-073987 | * | 4/2010 |
| KR | 10-0786947 B1 | | 12/2007 |

(Continued)

OTHER PUBLICATIONS

Translation for Jp 2010-073987 (publication date Apr. 2010).*

(Continued)

*Primary Examiner* — Dawn L. Garrett
(74) *Attorney, Agent, or Firm* — Robert E. Bushnell, Esq.

(57) ABSTRACT

An amine compound represented by Formula 1 below and an organic light-emitting device including an organic layer containing the same:

Formula 1

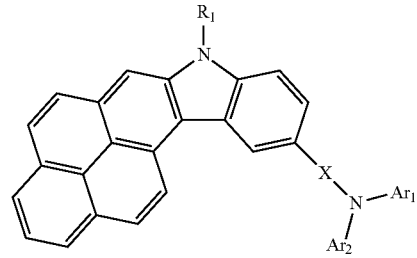

the compound of Formula 1 may be suitable as a hole injecting material, a hole transporting material, or a light-emitting material of an organic light-emitting device. Like the compound of Formula 1, a compound having a hetero ring in its molecular structure has a high glass transition temperature (Tg) or a high melting point due to the inclusion of the hetero ring. Accordingly, when light emission occurs, such a compound has high resistance against Joules' heat generated in an organic layer, between organic layers, and between an organic layer and a metallic electrode, and has high durability in high-temperature environments.

22 Claims, 2 Drawing Sheets

(56) References Cited

FOREIGN PATENT DOCUMENTS

| | | | |
|---|---|---|---|
| KR | 10-0793795 B1 | | 1/2008 |
| KR | 10-2009-0035729 A | | 4/2009 |
| KR | 10-2009-0042272 A | | 4/2009 |
| KR | 10-2009-0096393 A | | 9/2009 |
| KR | 10-2011-0034103 | | 4/2011 |
| WO | WO 2010114264 | * | 10/2010 |
| WO | 2011037429 A2 | | 3/2011 |
| WO | WO 2011037429 A2 | * | 3/2011 |

OTHER PUBLICATIONS

Korean Office action issued by KIPO on Mar. 26, 2012, corresponding to Korean Patent Application No. 10-2010-0067471 and Request for Entry attached herewith.

* cited by examiner

FIG. 2

An electrode material having a high work function is deposited or sputtered on a substrate to form a first electrode. The first electrode may constitute an anode or a cathode

An HIL is formed on the first electrode for example, by vacuum deposition, spin coating, casting, Langmuir-Blodgett (LB) deposition, or the like

An HTL is formed on the HIL for example, by vacuum deposition, spin coating, casting, LB deposition, or the like

An EML is formed on the HTL for example, by vacuum deposition, spin coating, casting, LB deposition, or the like

A hole blocking layer (HBL) may optionally be formed on the EML

An ETL is formed on the EML (or HBL) for example, by vacuum deposition, spin coating, casting, or the like

An EIL, which facilitates injection of electrons from the cathode, may be formed on the ETL

A second electrode is formed on the EIL by using, for example, vacuum deposition, sputtering, or the like

ORGANIC LIGHT-EMITTING DEVICE

CLAIM PRIORITY

This application claims the benefit of Korean Patent Application No. 10-2010-0067471, filed on Jul. 13, 2010, in the Korean Intellectual Property Office, the disclosure of which is incorporated herein in its entirety by reference.

BACKGROUND OF THE INVENTION

1. Field of the Invention

One or more embodiments of the present invention relate to an amine compound represented by Formula 1 and an organic light-emitting device including the same.

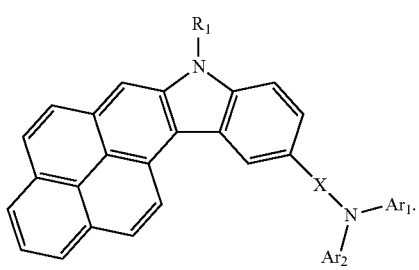

<Formula 1>

2. Description of the Related Art

Light-emitting devices are self-emission type display devices and have a wide viewing angle, a high contrast ratio, and short response times. Due to these characteristics, light-emitting devices are drawing more attention.

Among the light-emitting devices, organic light-emitting devices are roughly classified into inorganic light-emitting devices that include emission layers containing inorganic compounds, and organic light-emitting devices that include emission layers containing organic compounds.

Specifically, organic light-emitting devices have higher luminance, lower driving voltages, and shorter response times than inorganic light-emitting devices, and can render multi-colored displays. In addition, organic light-emitting devices produce various colors. Thus, much research into such organic light-emitting devices has been conducted.

Typically, organic light-emitting devices have a stack structure of anode/organic emitting layer/cathode, and a hole injection layer, a hole transport layer, an electron transport layer, or an electron injection layer may be further deposited between the anode and the emitting layer or the emitting layer and the cathode to form a structure of anode/hole transport layer/organic emitting layer/cathode, a structure of anode/hole transport layer/organic emitting layer/electron transport layer/cathode, or the like.

A material for forming the hole transport layer or the hole injection layer, is a polyphenyl compound or an anthracene derivative, for example. However, organic light-emitting devices manufactured using conventional materials for forming the hole transport layer and the hole injection layer have unsatisfactory lifetime, efficiency, and consumption power characteristics and such characteristics, need to be improved.

SUMMARY OF THE INVENTION

One or more embodiments of the present invention include an amine compound with improved electrical stability, charge-transporting capability, high glass transition temperature, and crystallization prevention capability.

One or more embodiments of the present invention include an organic light-emitting device including the amine compound.

One or more embodiments of the present invention include a flat panel display device including the organic light-emitting device.

One or more embodiments of the present invention include an organic light-emitting device including at least one organic layer containing the amine compound, wherein the at least one layer is formed using a wet process.

Additional aspects will be set forth in part in the description which follows and, in part, will be apparent from the description, or may be learned by practice of the presented embodiments.

According to one or more embodiments of the present invention, an amine compound represented by Formula 1 below;

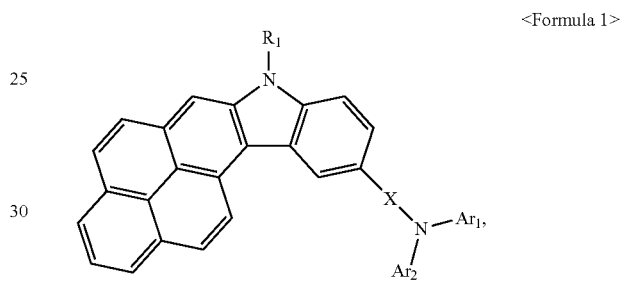

<Formula 1> wherein
$R_1$ is selected from the group consisting of a substituted or unsubstituted C1 to C60 alkyl group, a substituted or unsubstituted C3 to C60 cycloalkyl group, a substituted or unsubstituted C1 to C60 alkoxy group, a substituted or unsubstituted C5 to C60 aryloxy group, a substituted or unsubstituted C5 to C60 arylthio group, a substituted or unsubstituted C5 to C60 aryl group, a substituted or unsubstituted C3 to C60 heteroaryl group, and a substituted or unsubstituted C6 to C60 condensed polycyclic group, $Ar_1$ and $Ar_2$ are each independently selected from the group consisting of a substituted or unsubstituted C3 to C60 cycloalkyl group, a substituted or unsubstituted C5 to C60 aryloxy group, a substituted or unsubstituted C5 to C60 arylthio group, a substituted or unsubstituted C5 to C60 aryl group, a substituted or unsubstituted C3 to C60 heteroaryl group, and a substituted or unsubstituted C6 to C60 condensed polycyclic group, $Ar_1$ and $Ar_2$ may be linked to each other to form an aromatic ring, and X is a divalent linking group represented by $—(Ar_3)_n—$ where $Ar_3$ is one selected from the group consisting of a substituted or unsubstituted C5 to C60 arylene group, a substituted or unsubstituted C3 to C60 heteroarylene group, and a substituted or unsubstituted C6 to C60 condensed polycyclic group, n is an integer in the range of 0 through 10, the "n" groups of $Ar_3$ are identical to or different from each other, and among the "n" groups of $Ar_3$, two or more neighboring $Ar_3$ groups are fused with each other or linked to each other by a single bond.

In Formula 1, $R_1$ can also be selected from the group consisting of a substituted or unsubstituted C5 to C20 aryl group and a substituted or unsubstituted C6 to C20 condensed polycyclic group.

In Formula 1, $R_1$ can also be selected from the group consisting of a hydrogen atom, heavy hydrogen, a C1 to C20 alkyl group, and Formulae 2a and 2b below:

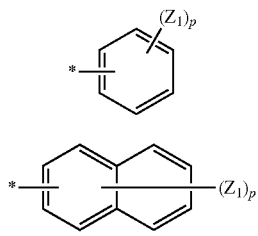

Formula 2a

Formula 2b in Formulae 2a and 2b, $Z_1$ is one selected from the group consisting of a hydrogen atom, heavy hydrogen, a C1 to C20 alkyl group, a C5 to C20 substituted or unsubstituted aryl group, a C3 to C20 substituted or unsubstituted heteroaryl group, a C6 to C20 substituted or unsubstituted condensed polycyclic group, a halogen atom, a cyano group, a nitro group, a hydroxyl group, and a carboxyl group;

p is an integer in the range of 1 through 8; and

* represents a bond.

In Formula 1, $R_1$ can also be selected from the group consisting of a methyl group, an ethyl group, a propyl group, a butyl group, a pentyl group, and Formulae 3a through 3c below:

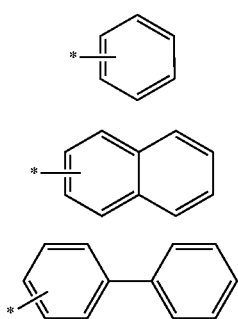

Formula 3a

Formula 3b

Formula 3c in Formulae 3a through 3c, * represents a bond.

In Formula 1, $Ar_1$ and $Ar_2$ can also be independently selected from the group consisting of a C1 to C20 alkyl group, a substituted or unsubstituted C5 to C20 aryl group, and a substituted or unsubstituted C3 to C20 heteroaryl group.

In Formula 1, $Ar_1$ or $Ar_2$ can also be selected from the group consisting of Formulae 4a through 4d:

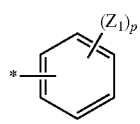

Formula 4a

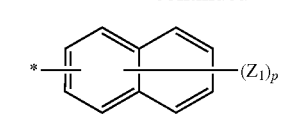

Formula 4b

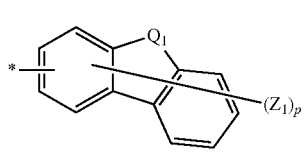

Formula 4c

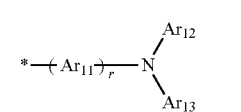

Formula 4d in Formulae 4a through 4d, $Q_1$ is one selected from the group consisting of linking groups represented by —$C(R_2)(R_3)$— and —$N(R_2)$—;

$Z_1$, $Ar_{12}$, $Ar_{13}$, $R_2$, and $R_3$ are each independently selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a halogen atom, a cyano group, a nitro group, a hydroxyl group, and a carboxyl group;

$Ar_{11}$ is one selected from the group consisting of a substituted or unsubstituted C1 to C20 alkylene group, a substituted or unsubstituted C5 to C20 arylene group, and a substituted or unsubstituted C3 to C20 heteroarylene group;

p is an integer in the range of 1 through 8;

r is an integer in the range of 1 through 5; and

* represents a bond.

In Formula 1, $Ar_1$ or $Ar_2$ can also be selected from the group consisting of Formulae 5a through 5f below:

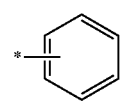

Formula 5a

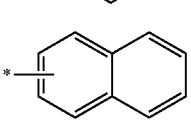

Formula 5b

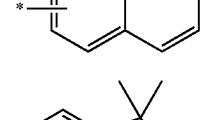

Formula 5c

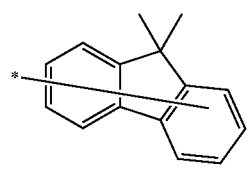

Formula 5d

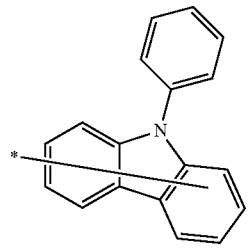

Formula 5e

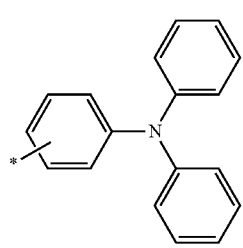

Formula 5f

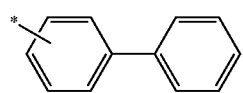

In Formulae 5a through 5f, * represents a bond.

$Ar_3$ can also be selected from the group consisting of a substituted or unsubstituted C5 to C20 arylene group, a substituted or unsubstituted C3 to C20 heteroarylene group, and a substituted or unsubstituted C6 to C20 condensed polycyclic group.

$Ar_3$ can also be selected from the group consisting of Formulae 6a through 6e:

Formula 6a

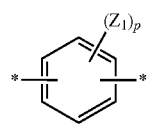

Formula 6b

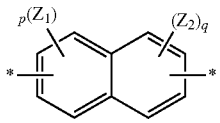

Formula 6c

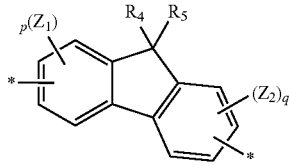

Formula 6d

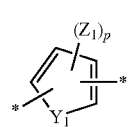

Formula 6e

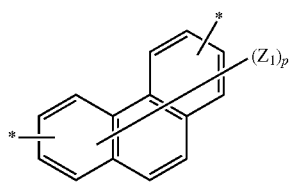

in Formulae 6a through 6e,
  $Y_1$ is one selected from the group consisting of linking groups represented by —S— and —O—;
  $Z_1$, $Z_2$, $R_4$, and $R_5$ are each independently one selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a halogen atom, a cyano group, a nitro group, a hydroxyl group, and a carboxyl group;
  p is an integer in the range of 1 through 10;
  q is an integer in the range of 1 through 8; and
  * represents a bond.

For —$(Ar_3)_n$—, "n" may also be 0 or 1.

In Formula 1, X is a single bond, or is selected from the group consisting of Formulae 7a through 7g below:

Formula 7a

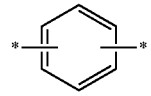

Formula 7b

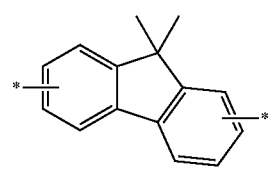

Formula 7c

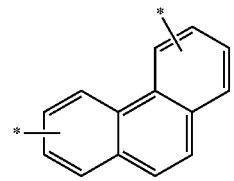

Formula 7d

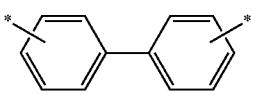

Formula 7e

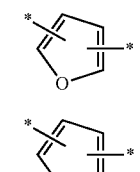

Formula 7f

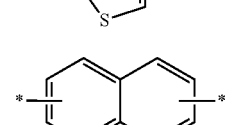

Formula 7g

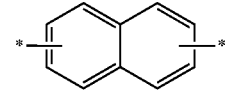

in Formulae 7a through 7g, * represents a bond.

In Formula 1,
  $R_1$ can also be selected from the group consisting of a methyl group, an ethyl group, a propyl group, a butyl group, a pentyl group, and Formulas 3a through 3c below:

Formula 3a

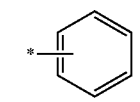

Formula 3b

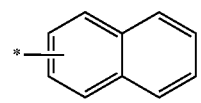

-continued

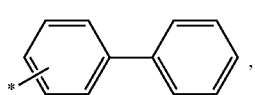
Formula 3c

Ar₁ or Ar₂ can also be selected from the group consisting of Formulae 5a through 5f below:

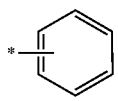
Formula 5a

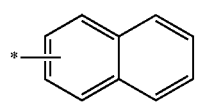
Formula 5b

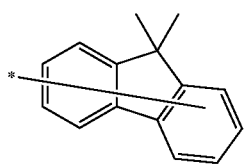
Formula 5c

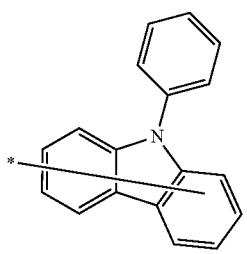
Formula 5d

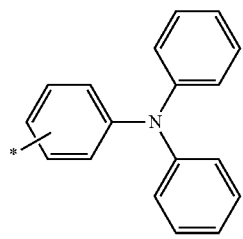
Formula 5e

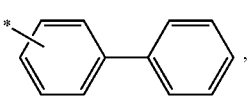
Formula 5f

X can also be a single bond or one selected from the group consisting of Formulae 7a through 7g:

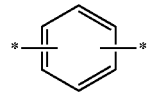
Formula 7a

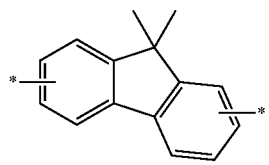
Formula 7b

-continued

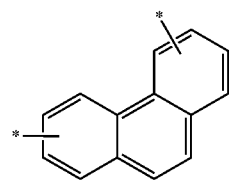
Formula 7c

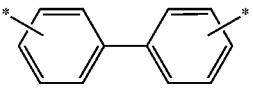
Formula 7d

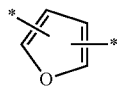
Formula 7e

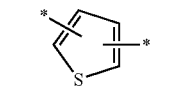
Formula 7f

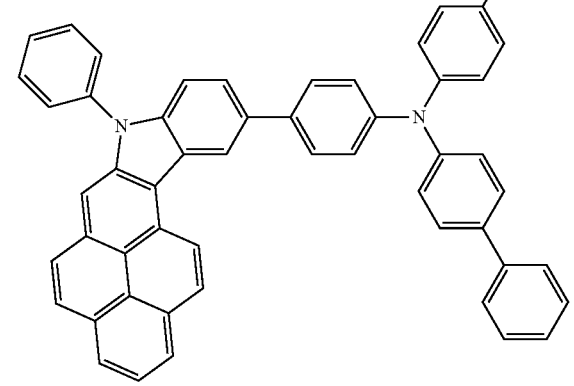
Formula 7g and in Formulas 3a through 3c, 5a through 5f, and 7a through 7g, * represents a bond.

The amine compound of Formula 1 can also be selected from the group consisting of compounds having following structures:

2

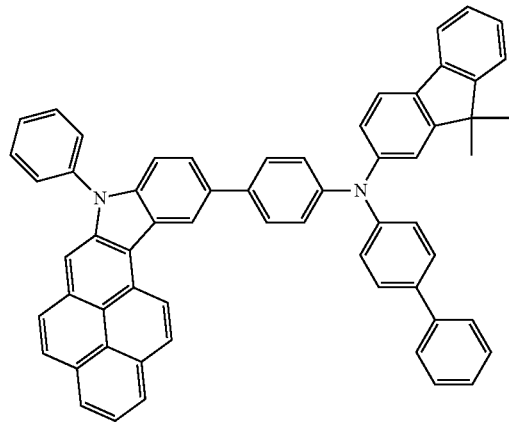

20

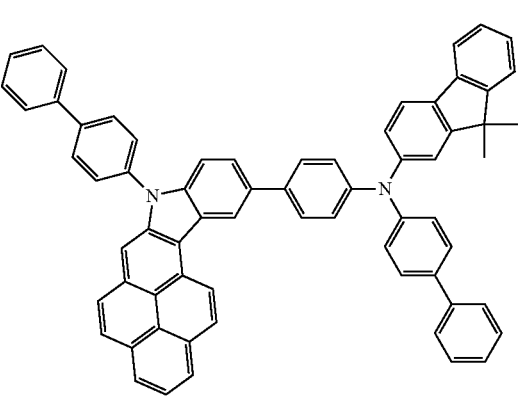

29

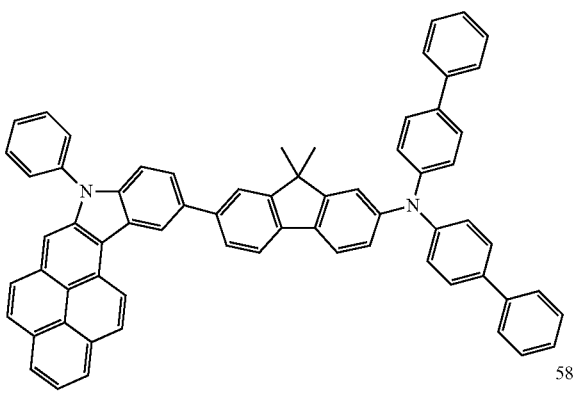

32

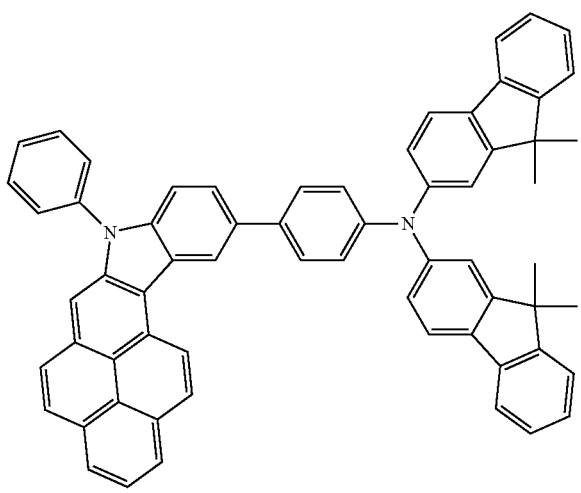

58

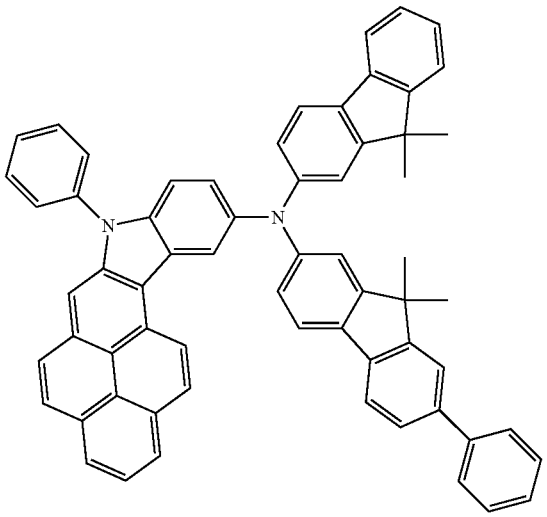

65

According to one or more embodiments of the present invention, an organic light-emitting device includes: a first electrode; a second electrode; and an organic layer interposed between the first electrode and the second electrode, wherein the organic layer includes the amine compound represented by Formula 1.

The organic layer may be a hole injection layer or a hole transport layer.

The organic layer may be a single layer having both hole injection and hole transport capabilities.

The organic layer is an emission layer, and the amine compound of Formula 1 is used as a host for a fluorescent or phosphorescent device.

The organic layer may be an emission layer, and the amine compound of Formula 1 is used as a fluorescent dopant.

The organic layer includes an emitting layer, a hole transport layer, and a hole injection layer, the emitting layer, the hole transport layer, or the hole injection layer includes the amine compound of Formula 1, and the emitting layer includes an anthracene compound, an arylamine compound, or a styryl compound.

The organic layer includes an emitting layer, a hole transport layer, and a hole injection layer, the emitting layer, the hole transport layer, or the hole injection layer includes the amine compound of Formula 1, and one layer selected from the group consisting of a red emitting layer, a green emitting layer, a blue emitting layer, and a white emission layer includes a phosphorescent compound.

The organic layer may be formed using a wet process.

According to one or more embodiments of the present invention, a flat panel display device includes the organic light-emitting device described above and the first electrode of the organic light-emitting device is electrically connected to a source electrode or a drain electrode of a thin film transistor.

BRIEF DESCRIPTION OF THE DRAWINGS

These and/or other aspects will become apparent and more readily appreciated from the following description of the embodiments, taken in connection with FIG. 1 which illustrates the structure of an organic light-emitting device according to an embodiment of the present invention.

FIG. 2 is a flow chart showing a method of making an organic light emitting device according to an embodiment of the present invention.

DETAILED DESCRIPTION

Figure 1:
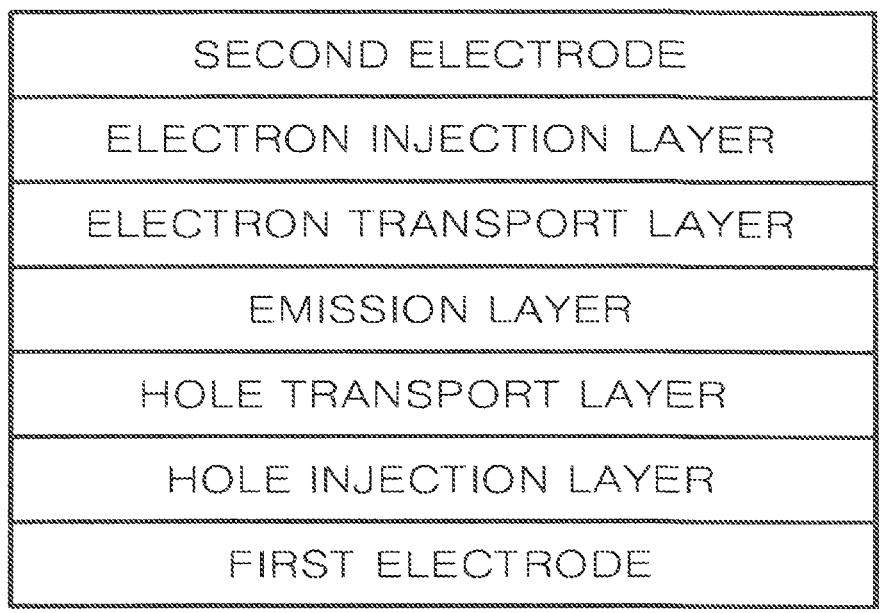

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

An amine compound according to an embodiment of the present invention may be represented by Formula 1 below:

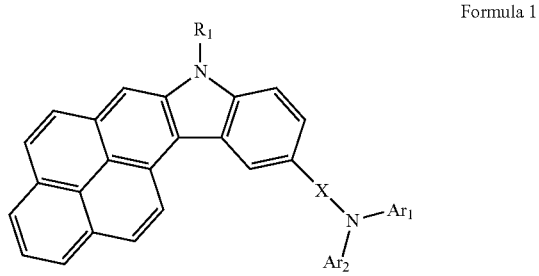

Formula 1 wherein
- $R_1$ is one selected from the group consisting of a substituted or unsubstituted C1 to C60 alkyl group, a substituted or unsubstituted C3 to C60 cycloalkyl group, a substituted or unsubstituted C1 to C60 alkoxy group, a substituted or unsubstituted C5 to C60 aryloxy group, a substituted or unsubstituted C5 to C60 arylthio group, a substituted or unsubstituted C5 to C60 aryl group, a substituted or unsubstituted C3 to C60 heteroaryl group, and a substituted or unsubstituted C6 to C60 condensed polycyclic group,
- $Ar_1$ and $Ar_2$ are each independently one selected from the group consisting of a substituted or unsubstituted C3 to C60 cycloalkyl group, a substituted or unsubstituted C5 to C60 aryloxy group, a substituted or unsubstituted C5 to C60 arylthio group, a substituted or unsubstituted C5 to C60 aryl group, a substituted or unsubstituted C3 to C60 heteroaryl group, and a substituted or unsubstituted C6 to C60 condensed polycyclic group,
- $Ar_1$ and $Ar_2$ may be linked to each other to form an aromatic ring, and
- X is a divalent linking group represented by $-(Ar_3)_n-$ where $Ar_3$ is one selected from the group consisting of a substituted or unsubstituted C5 to C60 arylene group, a substituted or unsubstituted C3 to C60 heteroarylene group, and a substituted or unsubstituted C6 to C60 condensed polycyclic group, n is an integer in the range of 0 through 10, the "n" groups of $Ar_3$ may be identical to or different from each other, and among the "n" groups of $Ar_3$, two or more neighboring $Ar_3$ groups may be fused with each other or linked to each other by a single bond.

The compound of Formula 1 may be suitable as a hole injecting material, a hole transporting material, or a light-emitting material of an organic light-emitting device. Like the compound of Formula 1, a compound having a hetero ring in its molecular structure has a high glass transition temperature (Tg) or a high melting point due to the inclusion of the hetero ring. Accordingly, when light emission occurs, such a compound has high resistance against Joules' heat generated in an organic layer, between organic layers, and between an organic layer and a metallic electrode, and has high durability in high-temperature environments.

An organic light-emitting device manufactured using the compound of Formula 1 has high durability during preservation and operation. In addition, due to the inclusion of a substituent such as an aryl group or heteroaryl group, molecular layers formed as thin films may be maintained in good condition, thereby improving the characteristics of the organic light-emitting device.

Substituents of the compound of Formula 1 will now be described in detail.

In Formula 1, $R_1$ may be one selected from the group consisting of a C5 to C20 aryl group and a C6 to C20 condensed polycyclic group. The aryl group or the condensed polycyclic group may be an aryl group or a condensed polycyclic group substituted with a substituent such as those which will be described in connection with the C1 to C60 alkyl group. Hereinafter, the term "substituted" means substitution with a substituent such as those which will be described in connection with the C1 to C60 alkyl group, unless otherwise defined.

For example, In Formula 1, $R_1$ may be selected from the group consisting of a hydrogen atom, heavy hydrogen, a C1 to C20 alkyl group, and Formulae 2a and 2b:

Formula 2a

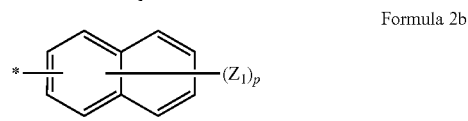

Formula 2b

In Formulae 2a and 2b, $Z_1$ may be one selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a halogen atom, a cyano group, a nitro group, a hydroxyl group, and a carboxyl group; p is an integer in the range of 1 through 8; and * represents a bond.

For example, in Formula 1, $R_1$ may be one selected from the group consisting of a methyl group, an ethyl group, a propyl group, a butyl group, a pentyl group, and Formulae 3a through 3c:

Formula 3a

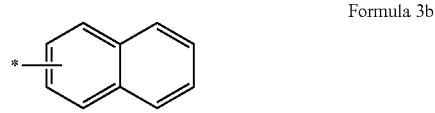

Formula 3b

-continued

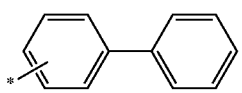

Formula 3c

In Formulae 3a through 3c, * represents a bond.

In Formula 1, $Ar_1$ and $Ar_2$ may be each independently one selected from the group consisting of a C1 to C20 alkyl group, a substituted or unsubstituted C5 to C20 aryl group, and a substituted or unsubstituted C3 to C20 heteroaryl group, for example, one selected from the group consisting of Formulae 4a through 4d below:

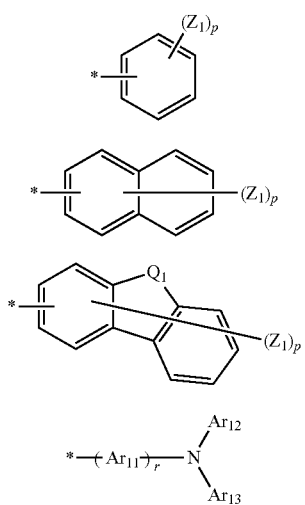

Formula 4a

Formula 4b

Formula 4c

Formula 4d

In Formulae 4a through 4d, $Q_1$ is one selected from the group consisting of linking groups represented by —$C(R_2)(R_3)$— and —$N(R_2)$—; $Z_1$, $Ar_{12}$, $Ar_{13}$, $R_2$ and $R_3$ are each independently one selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a, halogen atom, a cyano group, a nitro group, a hydroxyl group, and a carboxyl group; $Ar_{11}$ is one selected from the group consisting of a substituted or unsubstituted C1 to C20 alkylene group, a substituted or unsubstituted C5 to C20 arylene group, and a substituted or unsubstituted C3 to C20 heteroarylene group; p is an integer in the range of 1 through 8; r is an integer in the range of 1 through 5; and * represents a bond.

For example, In Formula 1, $Ar_1$ or $Ar_2$ may be one selected from the group consisting of Formulae 5a through 5f:

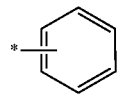

Formula 5a

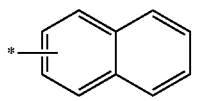

Formula 5b

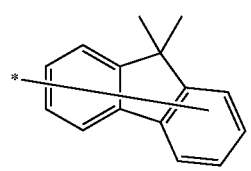

Formula 5c

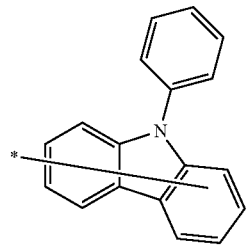

Formula 5d

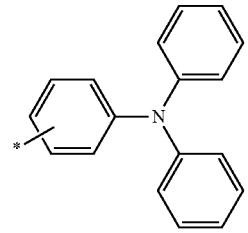

Formula 5e

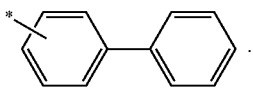

Formula 5f

In Formulae 5a through 5f, * represents a bond.

$Ar_3$ may be one selected from the group consisting of a substituted or unsubstituted C5 to C20 arylene group, a substituted or unsubstituted C3 to C20 heteroarylene group, and a substituted or unsubstituted C6 to C20 condensed polycyclic group.

For example, $Ar_3$ may be one selected from the group consisting of Formulae 6a through 6e:

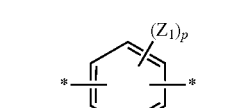

Formula 6a

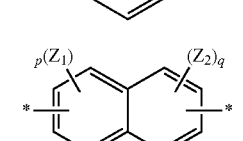

Formula 6b

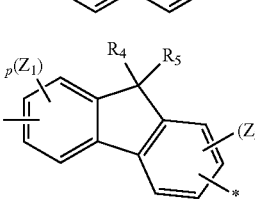

Formula 6c

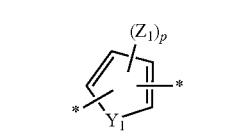

Formula 6d

-continued

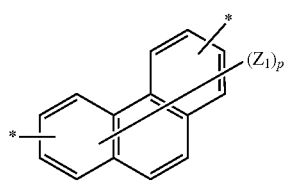
Formula 6e

In Formula 6a through 6e, $Y_1$ is one selected from the group consisting of linking groups represented by —S— and —O—; $Z_1$, $Z_2$, $R_4$, and $R_5$ are each independently one selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a halogen atom, a cyano group, a nitro group, a hydroxyl group, and a carboxyl group; p is an integer in the range of 1 through 10; q is an integer in the range of 1 through 8; and * represents a bond.

Meanwhile, in —$(Ar_3)_n$— "n" may be 0 or 1.

In Formula 1, X may be a single bond or one selected from the group consisting of Formulae 7a through 7g:

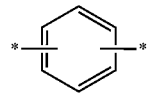
Formula 7a

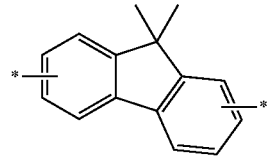
Formula 7b

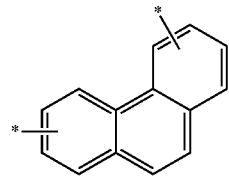
Formula 7c

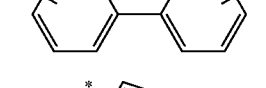
Formula 7d

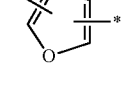
Formula 7e

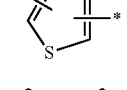
Formula 7f

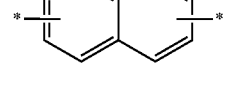
Formula 7g

In Formulae 7a through 7g, * represents a bond.

In Formula 1, $R_1$ may be one selected from the group consisting of a methyl group, an ethyl group, a propyl group, a butyl group, a pentyl group, and Formulae 3a through 3c below,

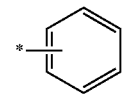
Formula 3a

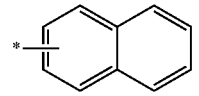
Formula 3b

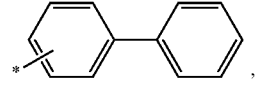
Formula 3c $Ar_1$ or $Ar_2$ may be one selected from the group consisting of Formulae 5a through 5f, and

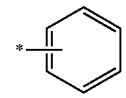
Formula 5a

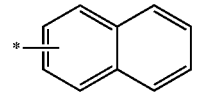
Formula 5b

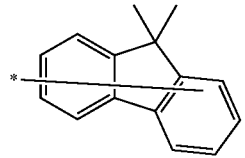
Formula 5c

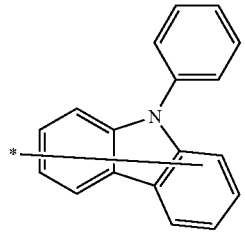
Formula 5d

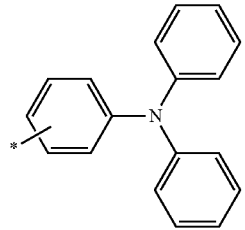
Formula 5e

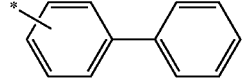
Formula 5f

X may be a single bond or one selected from the group consisting of Formulae 7a through 7g:

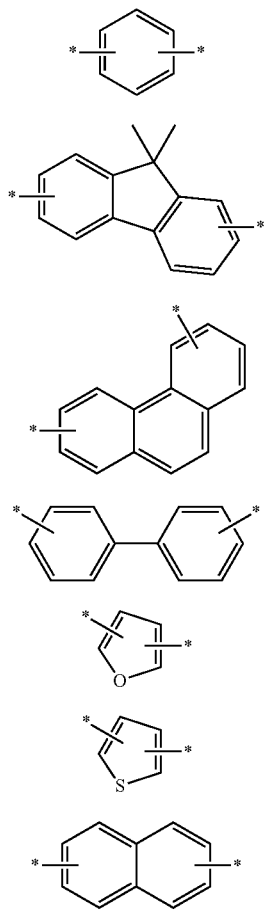

Formula 7a

Formula 7b

Formula 7c

Formula 7d

Formula 7e

Formula 7f

Formula 7g

In Formulae 3a through 3c, 5a through 5f, and 7a through 7g, * represents a bond.

Hereinafter, substituents described with reference to formulae used herein will now be described in detail. In this regard, the numbers of carbons in substituents are presented only for illustrative purposes and do not limit the characteristics of the substituents.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_5$-$C_{16}$ aryl group, or a $C_3$-$C_{16}$ heteroaryl group.

The unsubstituted $C_3$-$C_{60}$ cycloalkyl group used herein refers to a $C_3$-$C_{60}$ cyclic alkyl group wherein at least one hydrogen atom in the cycloalkyl group may be substituted with a substituent such as those described above in connection with the $C_1$-$C_{60}$ alkyl group.

The unsubstituted $C_1$-$C_{60}$ alkoxy group used herein is a group having a structure of —OA wherein A is an unsubstituted $C_1$-$C_{60}$ alkyl group as described above. Examples of the unsubstituted $C_1$-$C_{60}$ alkoxy group include, but are not limited to, a methoxy group, an ethoxy group, a propoxy group, an isopropyloxy group, a butoxy group, and a pentoxy group. At least one hydrogen atom of the alkoxy group may also be substituted with a substituent such as those described above in connection with the $C_1$-$C_{60}$ alkyl group.

The unsubstituted $C_5$-$C_{60}$ aryl group used herein refers to a carbocyclic aromatic system containing at least one ring. When the carbocyclic aromatic system includes at least two rings, the rings may be fused to each other or linked to each other by a single bond. The term 'aryl' refers to an aromatic system, such as phenyl, naphthyl, or anthracenyl. At least one hydrogen atom in the aryl group may also be substituted with a substituent such as those described above in connection with the $C_1$-$C_{60}$ alkyl group.

Examples of the substituted or unsubstituted $C_5$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group includes one, two or three hetero atoms selected from N, O, P, and S. When the unsubstituted $C_3$-$C_{60}$ heteroaryl group includes at least two rings, the rings may be fused to each other or linked to each other by a single bond. Examples of the unsubstituted $C_3$-$C_{60}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent such as those described above in connection with the $C_1$-$C_{60}$ alkyl group.

The unsubstituted C5 to $C_{60}$ aryloxy group is a group represented by —$OA_1$ where $A_1$ is a C5 to C60 aryl group. An example of the aryloxy group is a phenoxy group. At least one hydrogen atom in the aryloxy group may also be substituted with a substituent such as those described above in connection with the $C_1$-$C_{60}$ alkyl group.

The C5 to $C_{60}$ unsubstituted arylthio group is a group represented by —$SA_1$ where $A_1$ is a C5 to C60 aryl group. An example of the arylthio group is a benzenethio group or a naphthylthio group. At least one hydrogen atom in the arylthio group may also be substituted with a substituent such as those described above in connection with the $C_1$-$C_{60}$ alkyl group.

The unsubstituted $C_6$-$C_{60}$ condensed polycyclic group used herein refers to a substituent including at least two rings wherein at least one aromatic ring and/or at least one non-aromatic ring are fused to each other.

In addition, at least one hydrogen atom in the condensed polycyclic group may be substituted with a substituent such as those described above in connection with the $C_1$-$C_{60}$ alkyl group.

Examples of the amine compound represented by Formula 1 may include Compounds 1 through 72 represented by the following structures. However, the compounds represented by Formula 1 are not limited thereto.

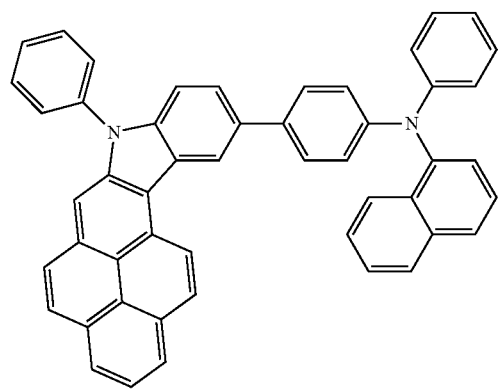

1

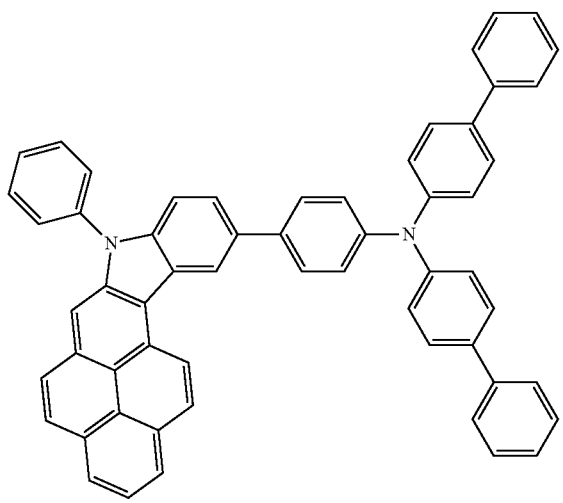

2

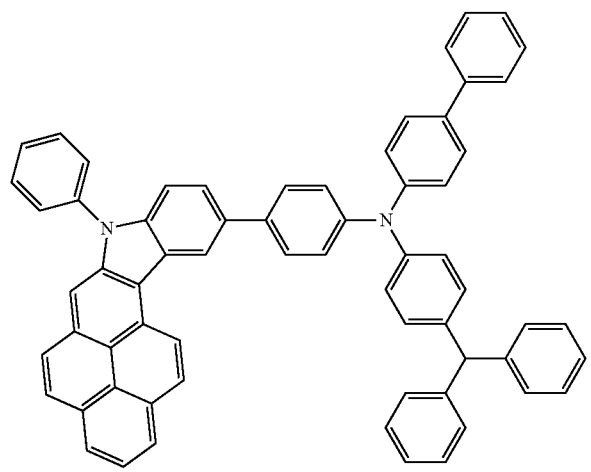

3

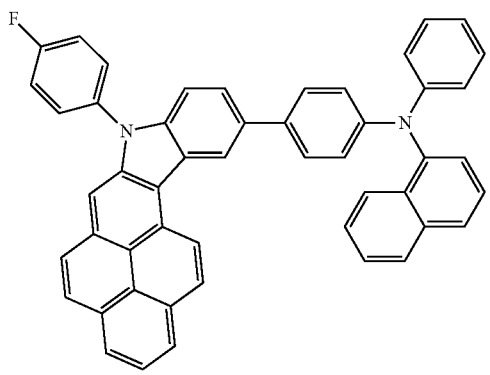

4

5
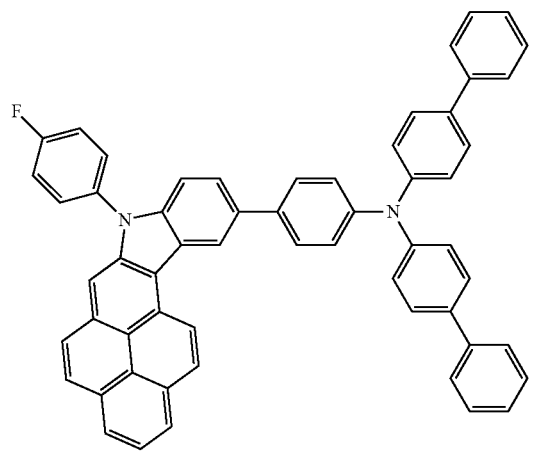
6
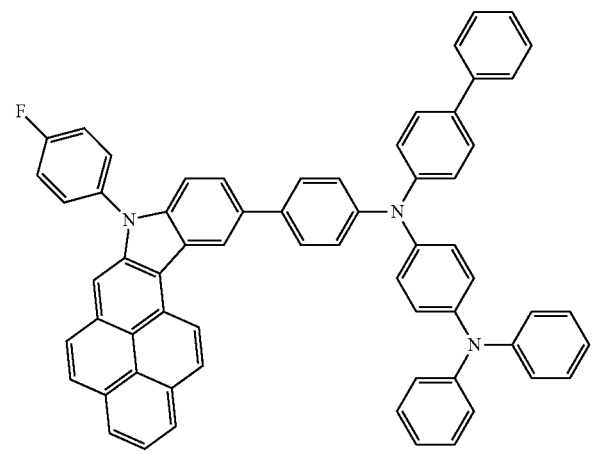
7
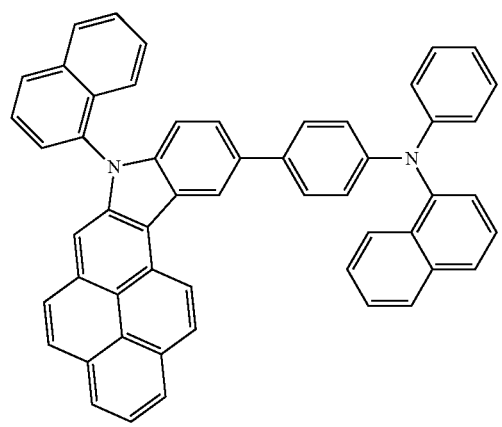
8
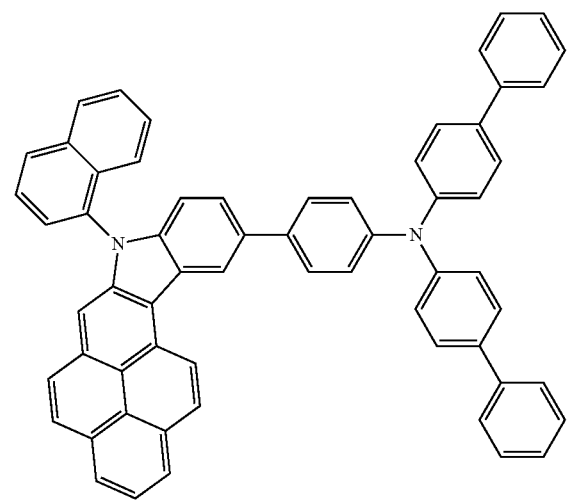
9
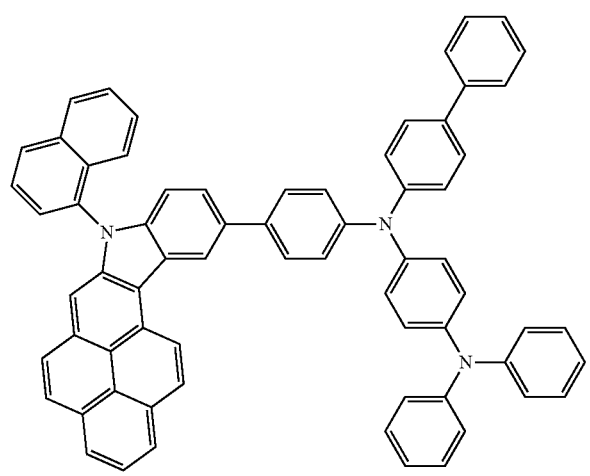
10
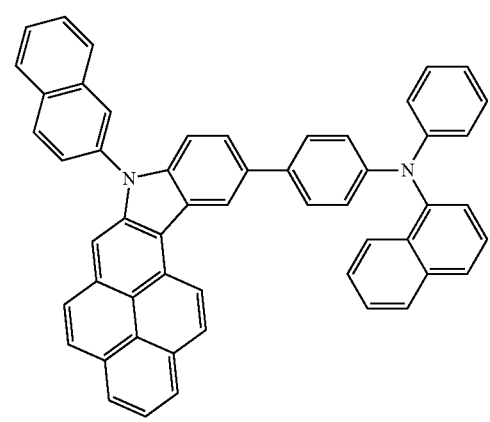

-continued
11
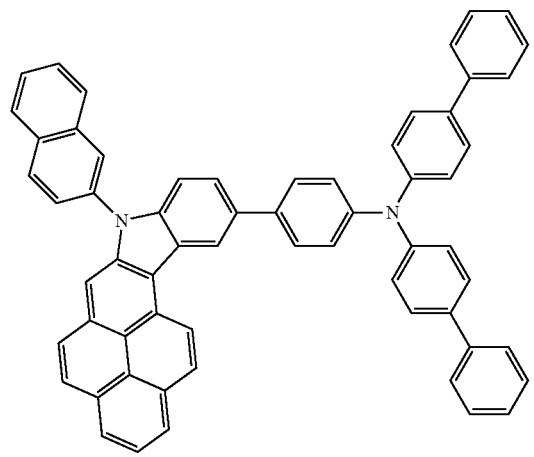
12
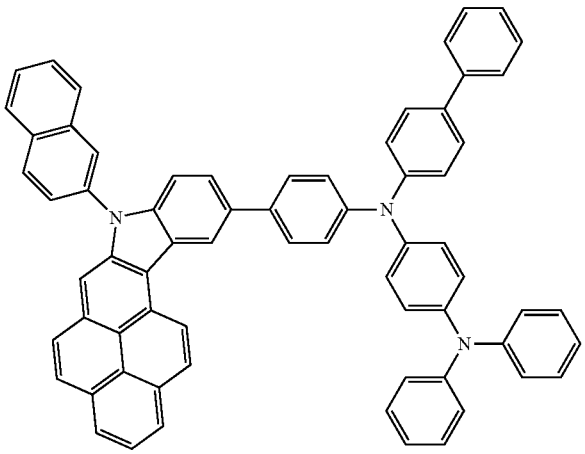
13
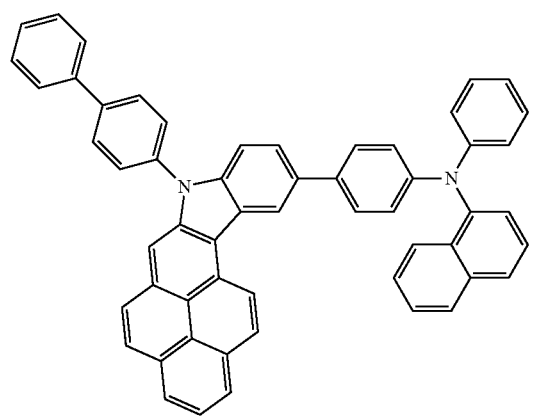
14
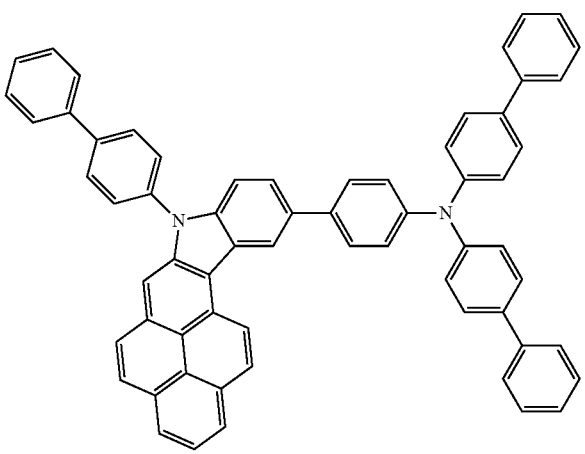
15
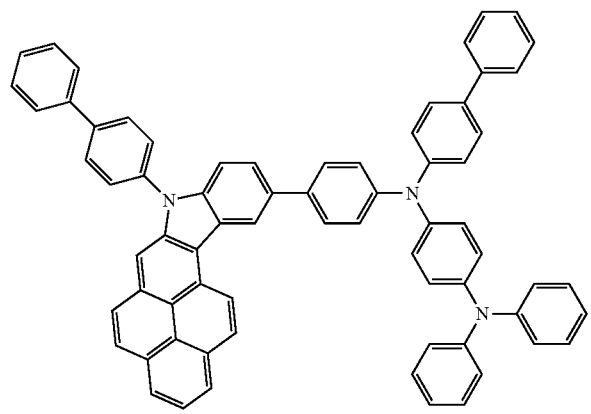
16
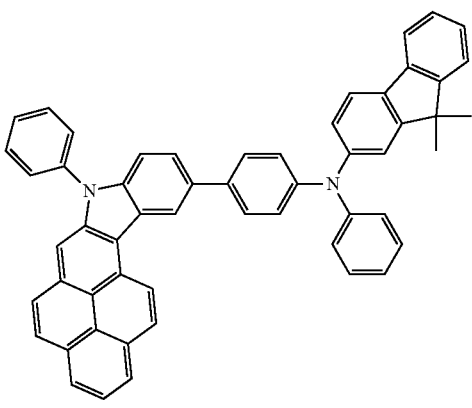

-continued
17
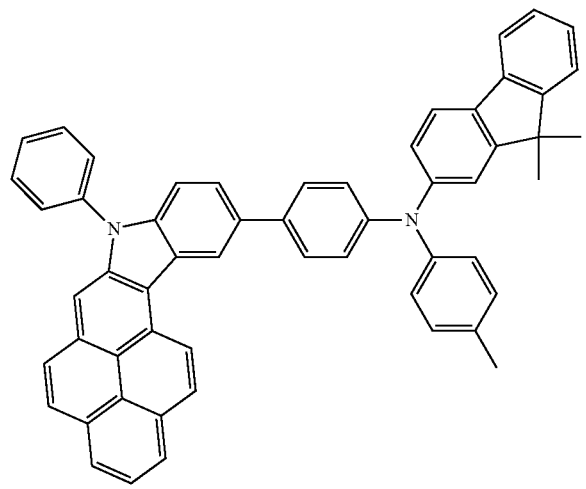
18
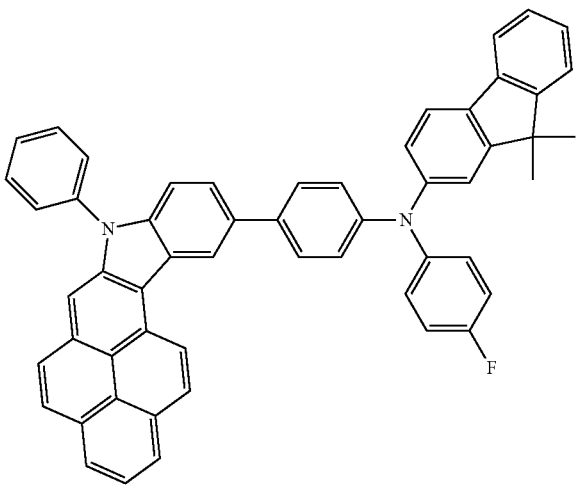
19
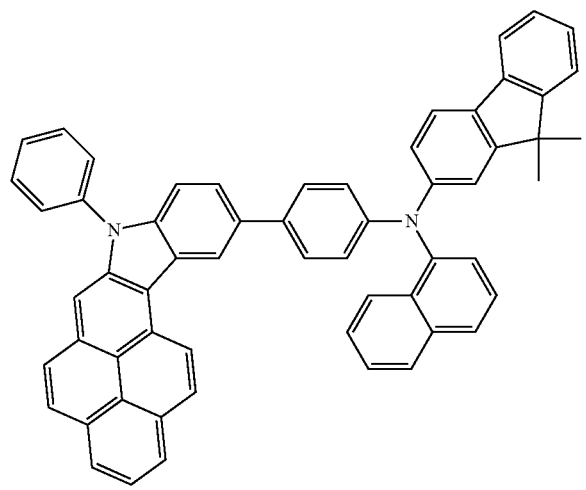
20
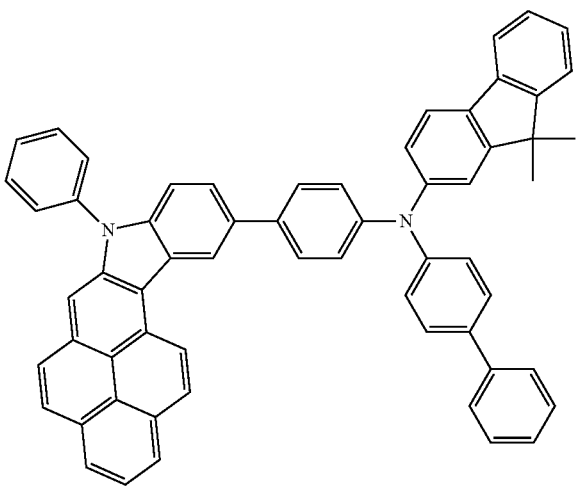
21
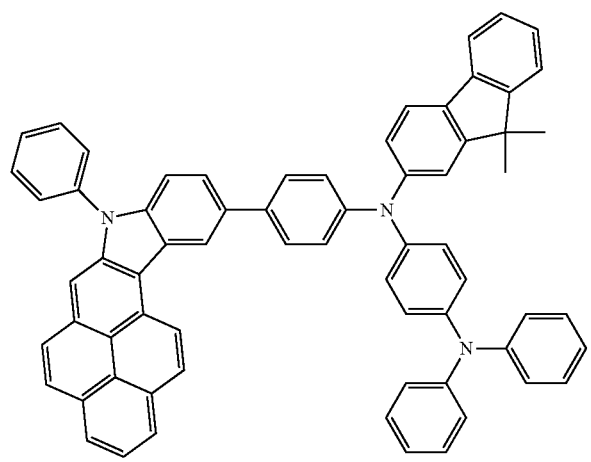
22
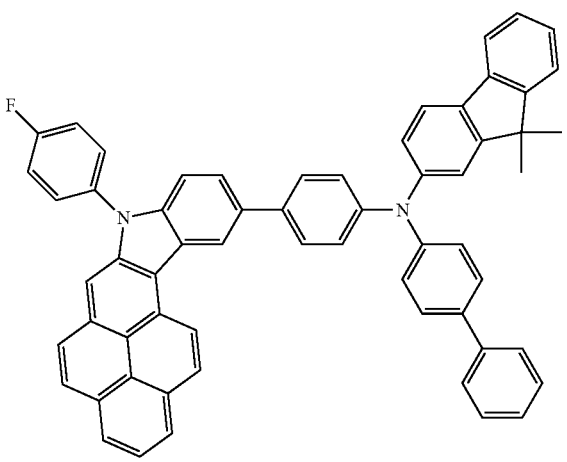

-continued
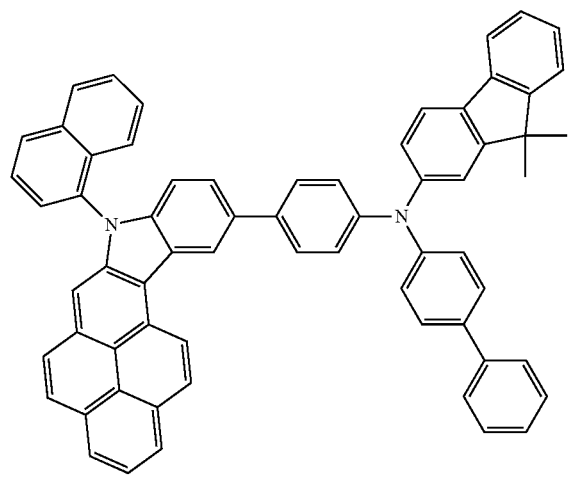
23
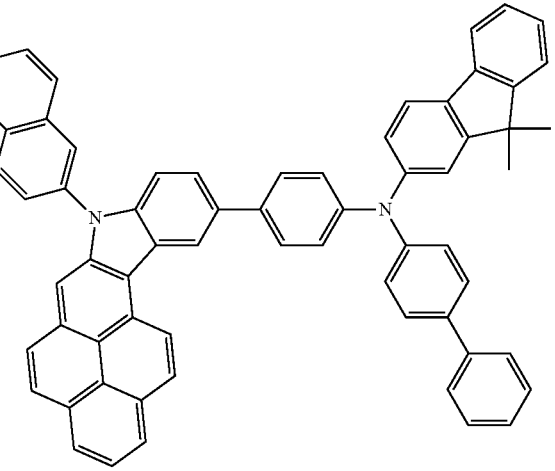
24
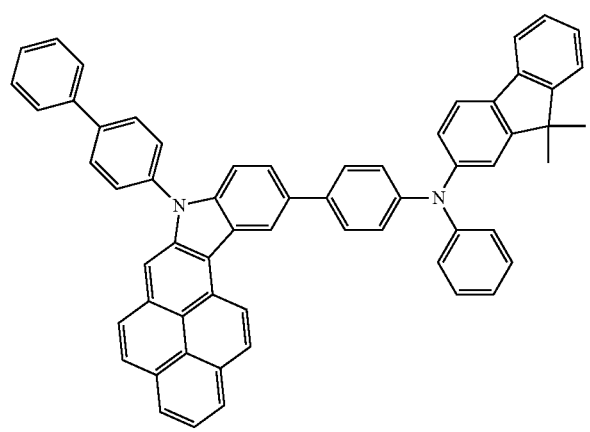
25
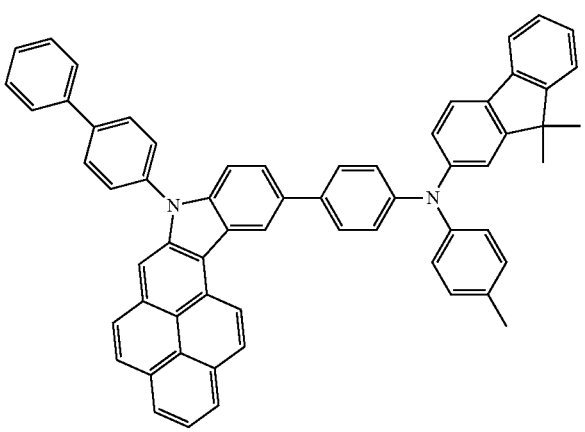
26
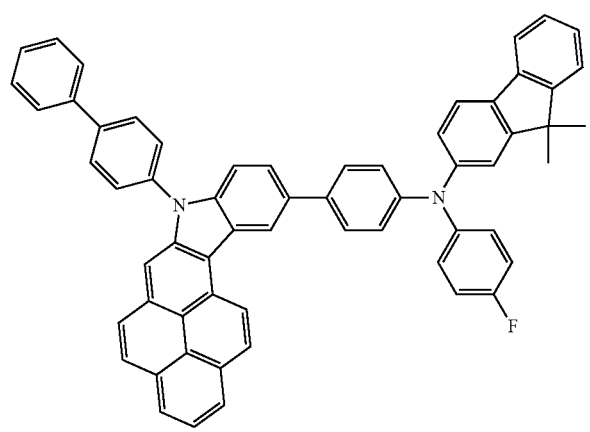
27
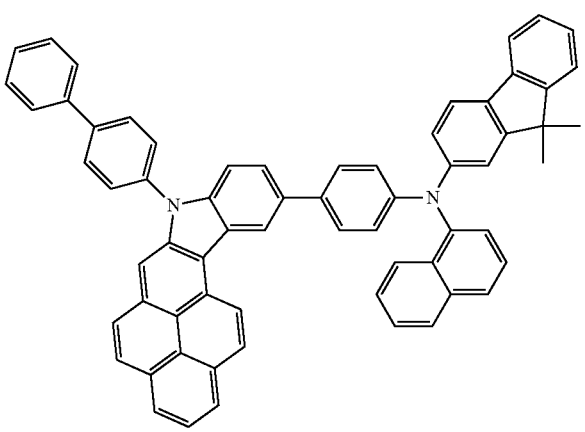
28

-continued
29
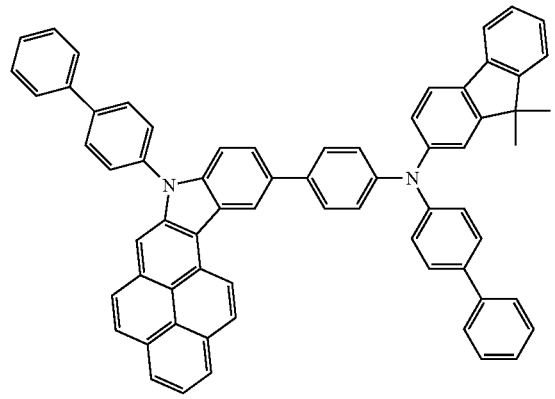
30
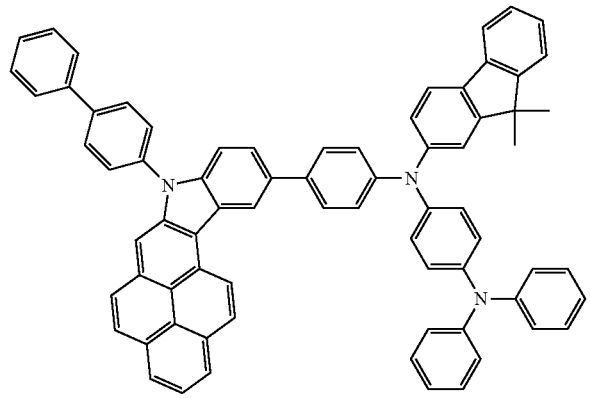
31
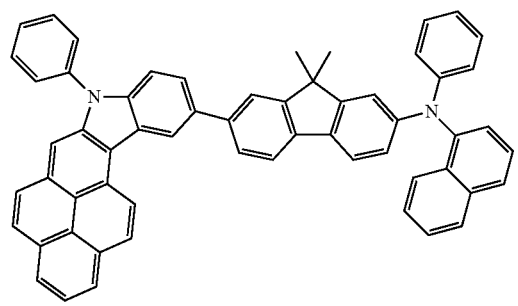
32
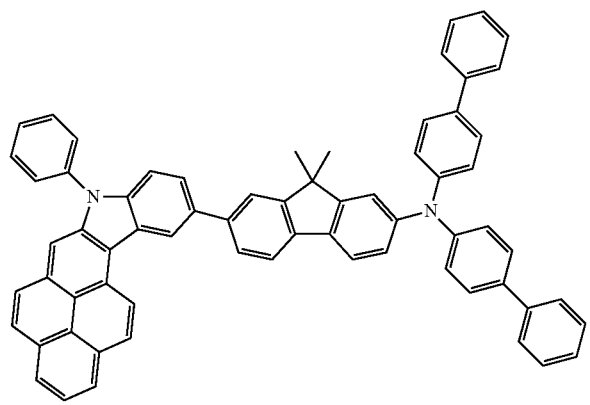
33
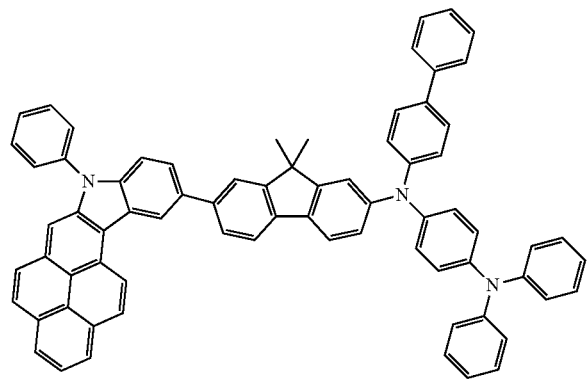
34
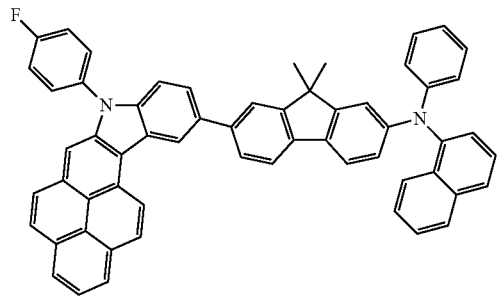

35
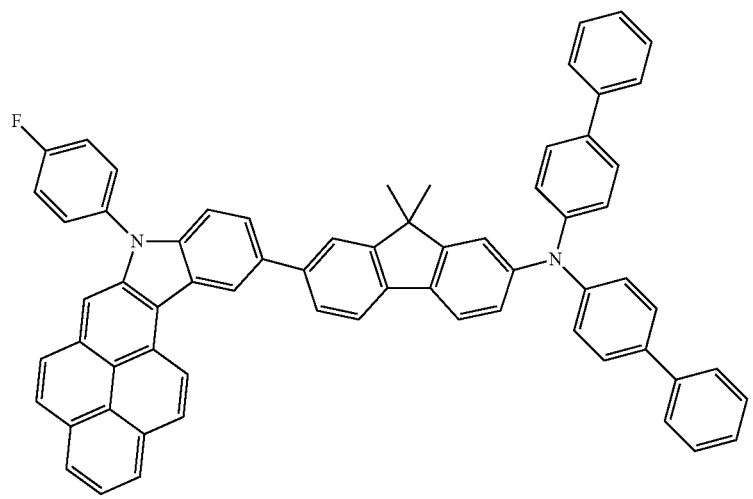
36
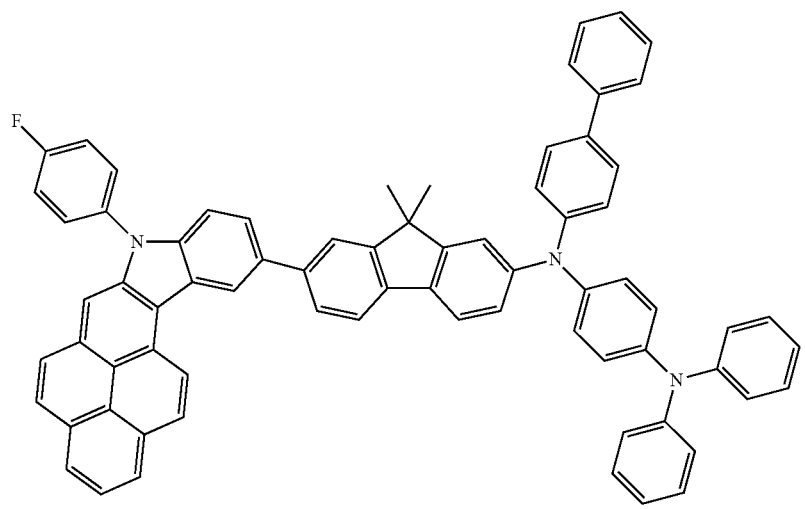
37
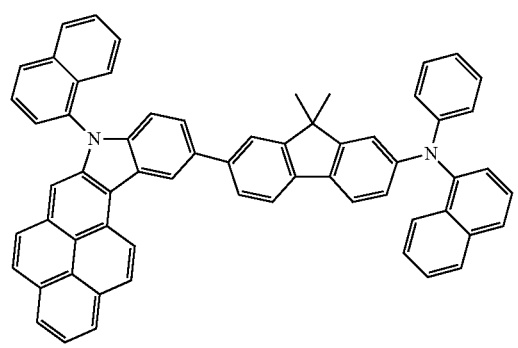
38
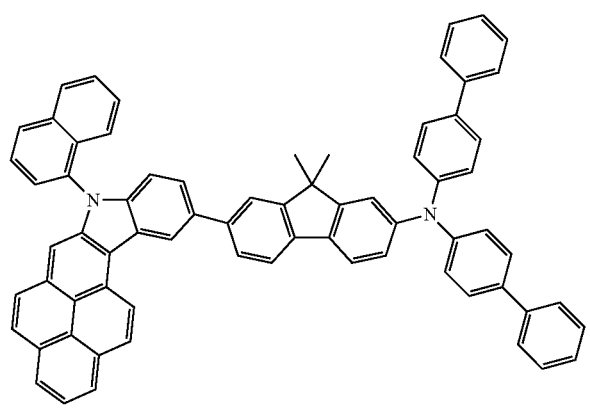

39
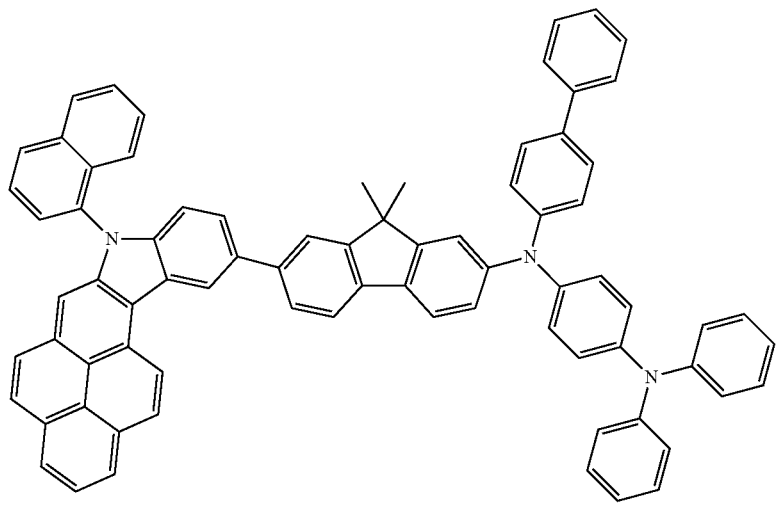
40
41
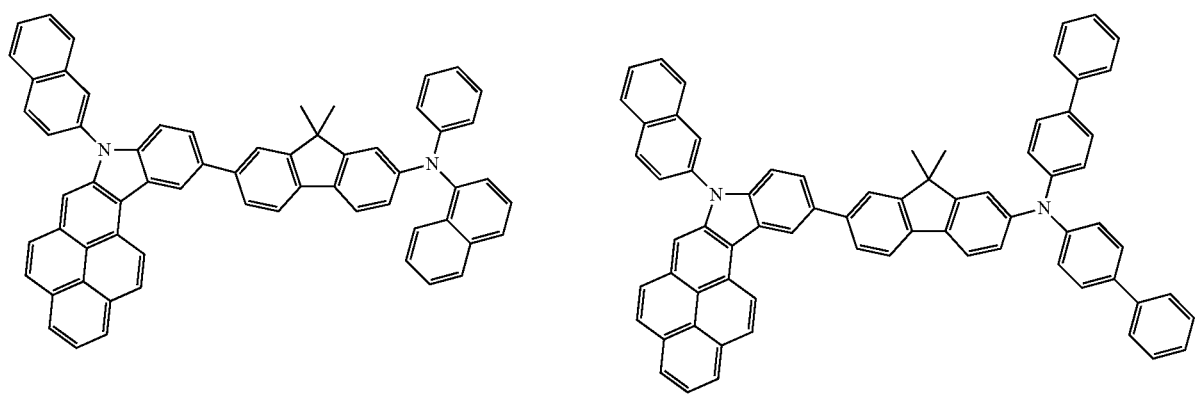
42
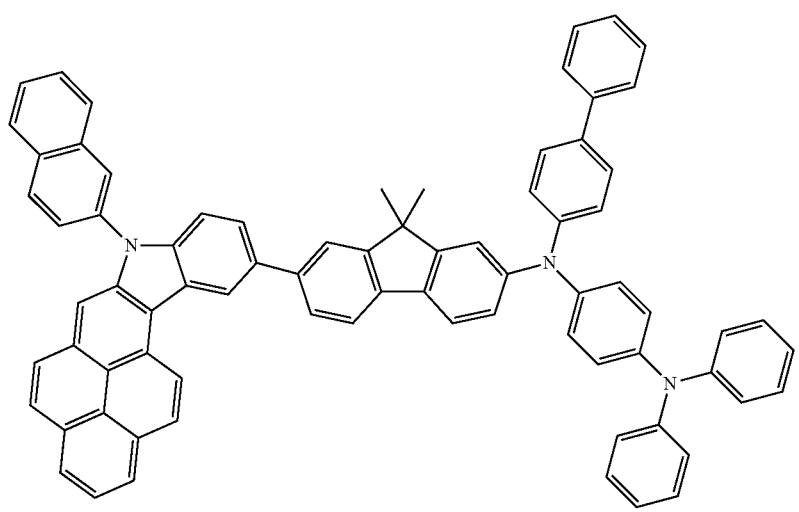

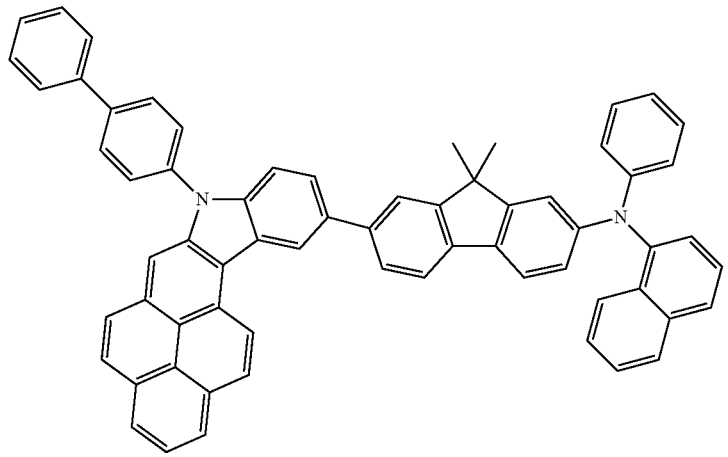
43
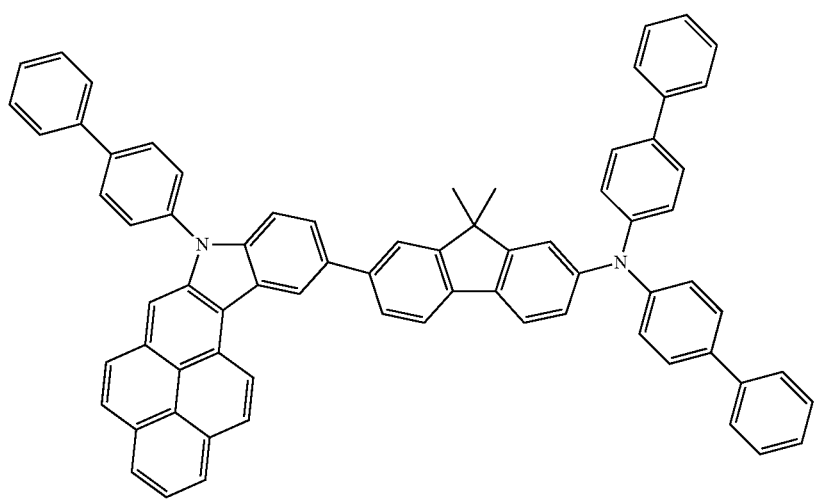
44
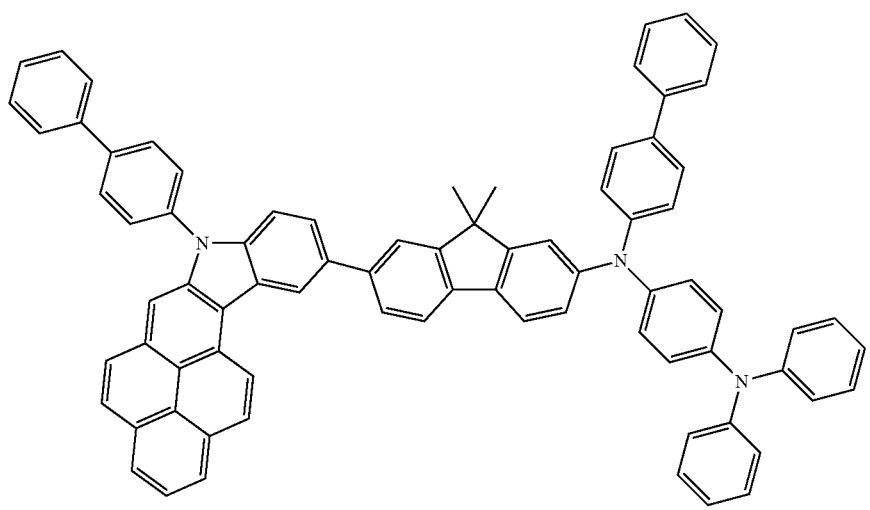
45

46
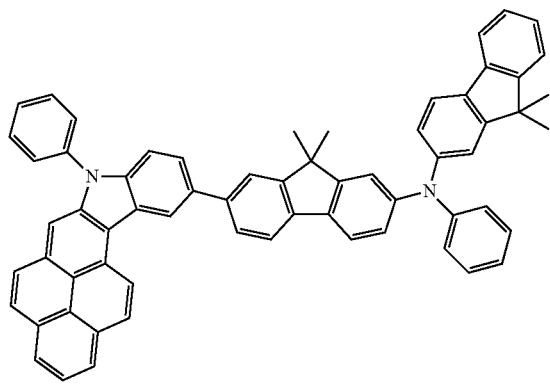
47
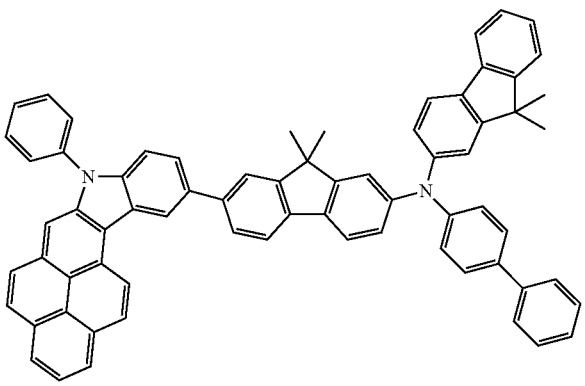
48
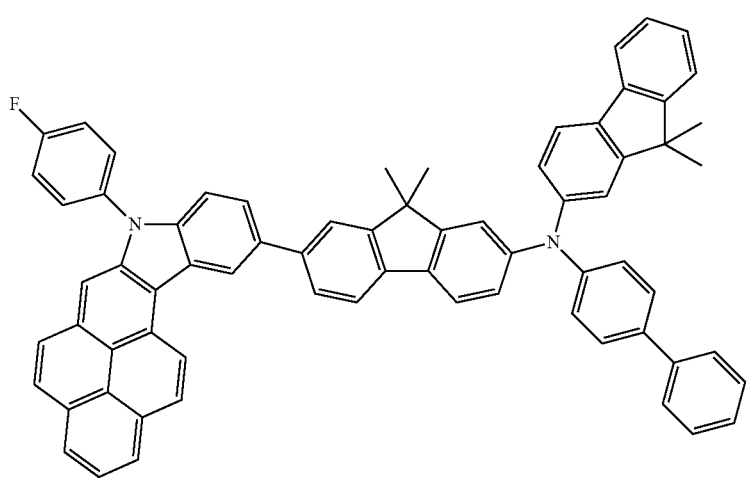
49
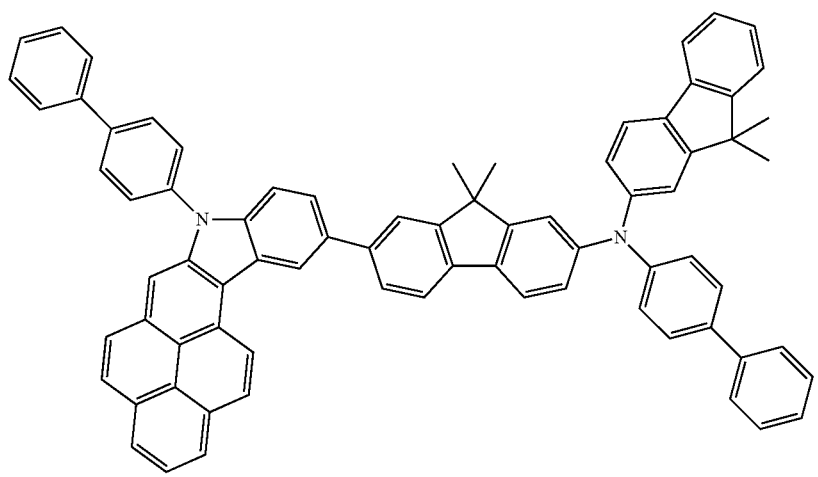

50
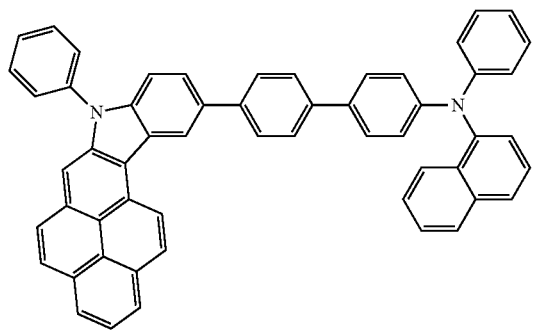
51
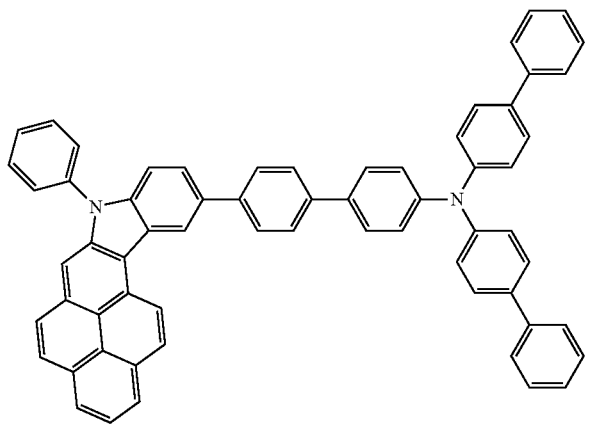
52
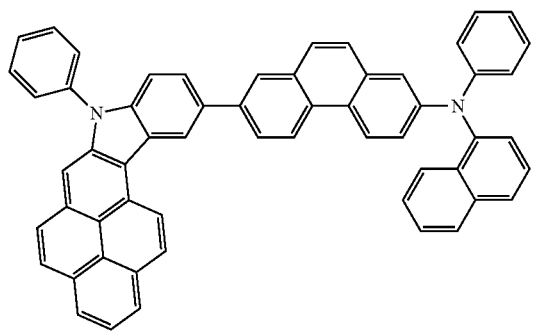
53
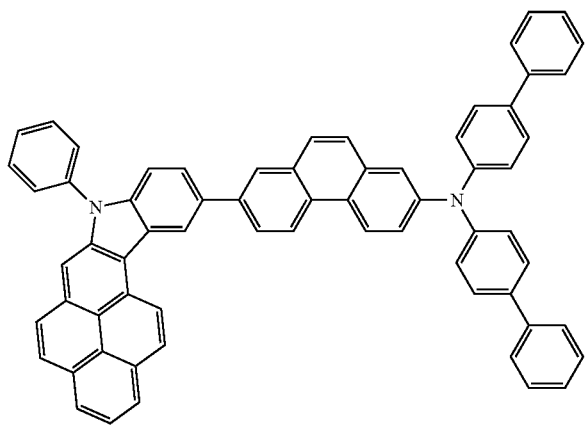
54
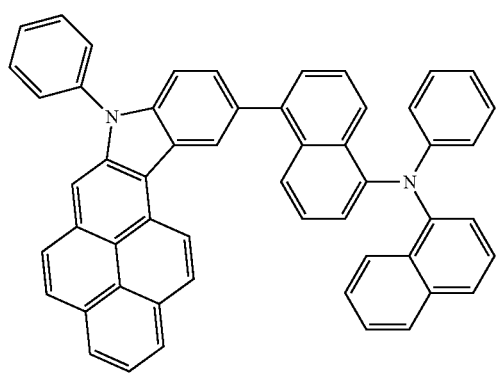
55
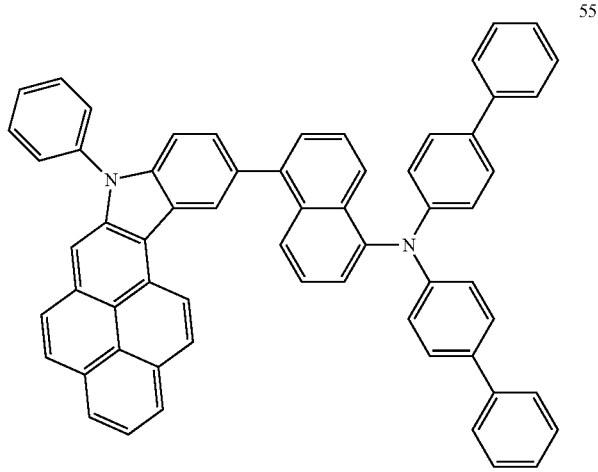

-continued
56
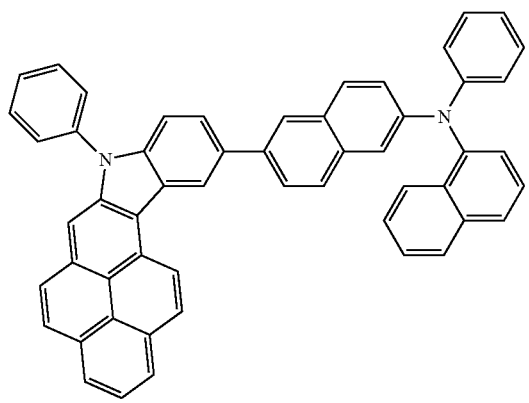
57
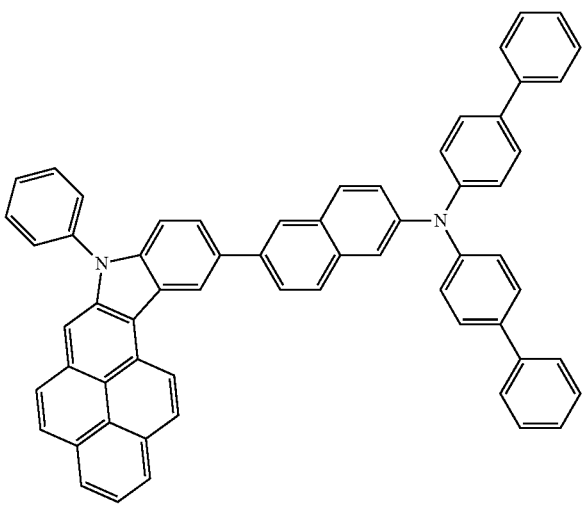
58
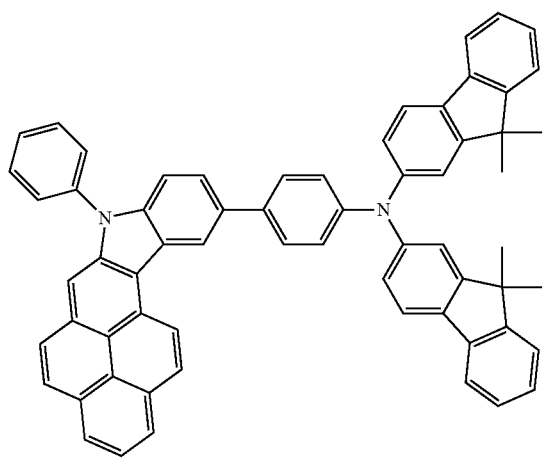
59
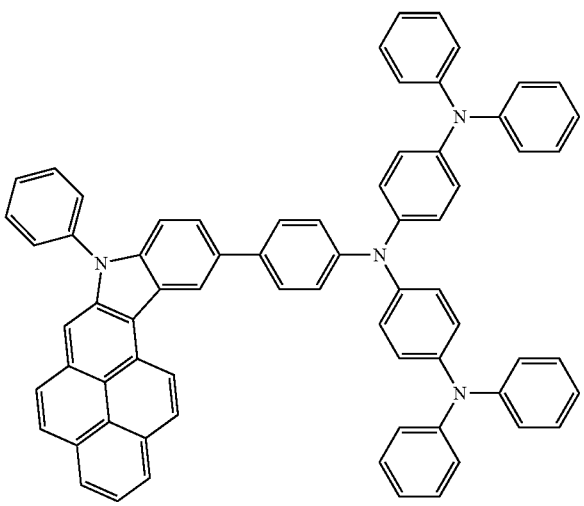
60
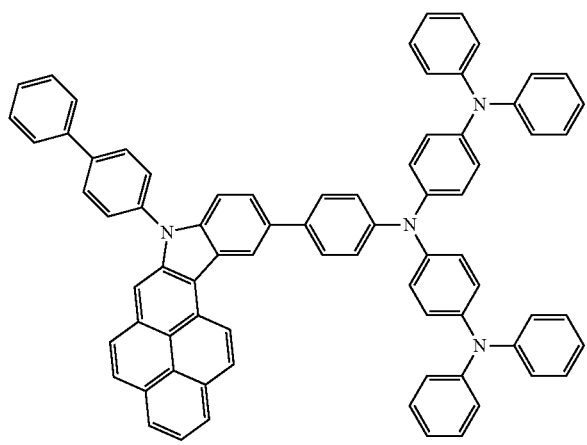
61
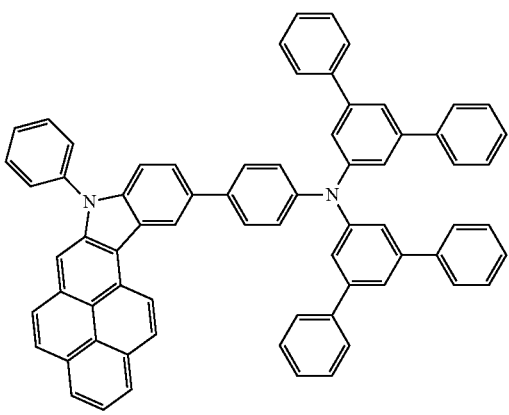

-continued
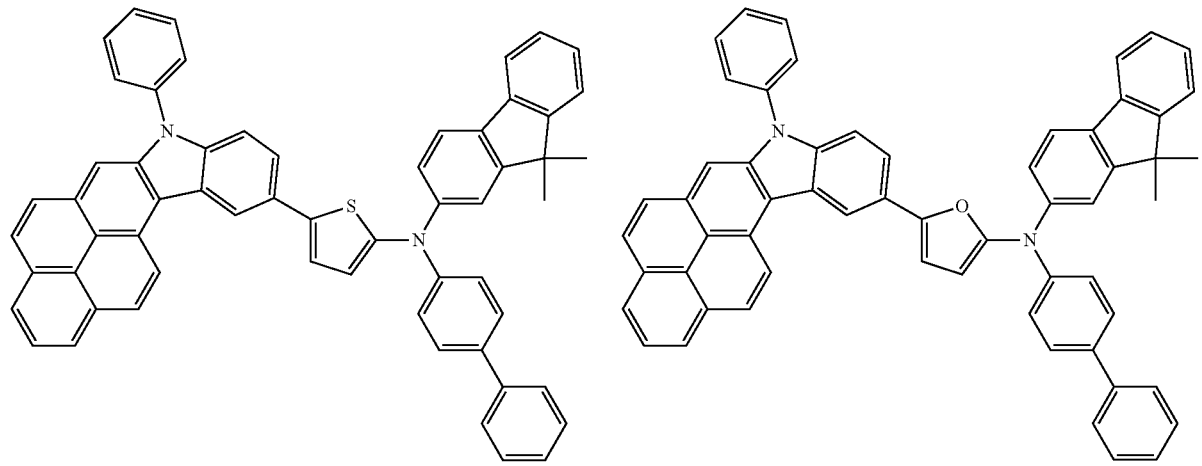
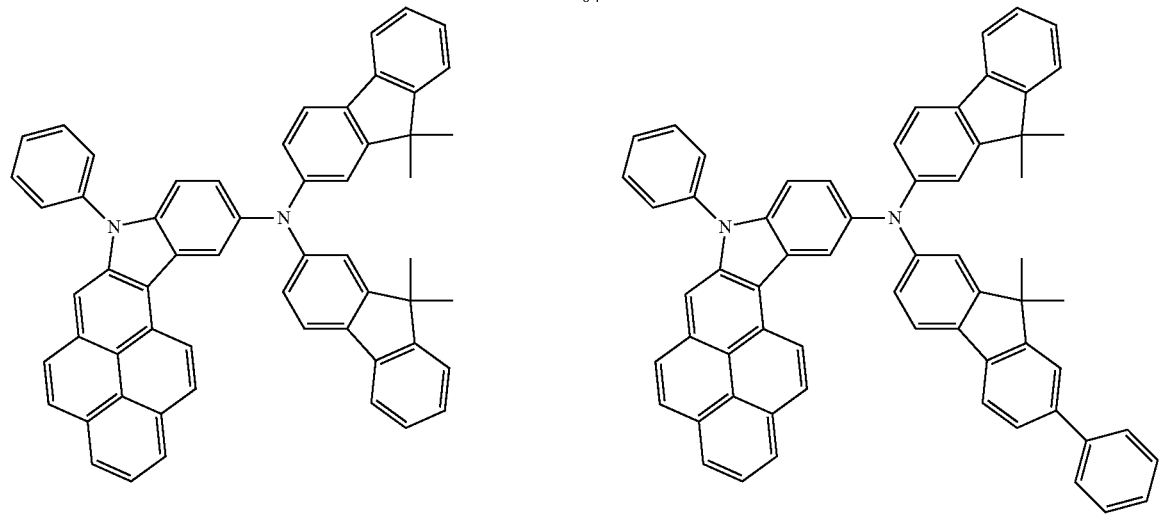
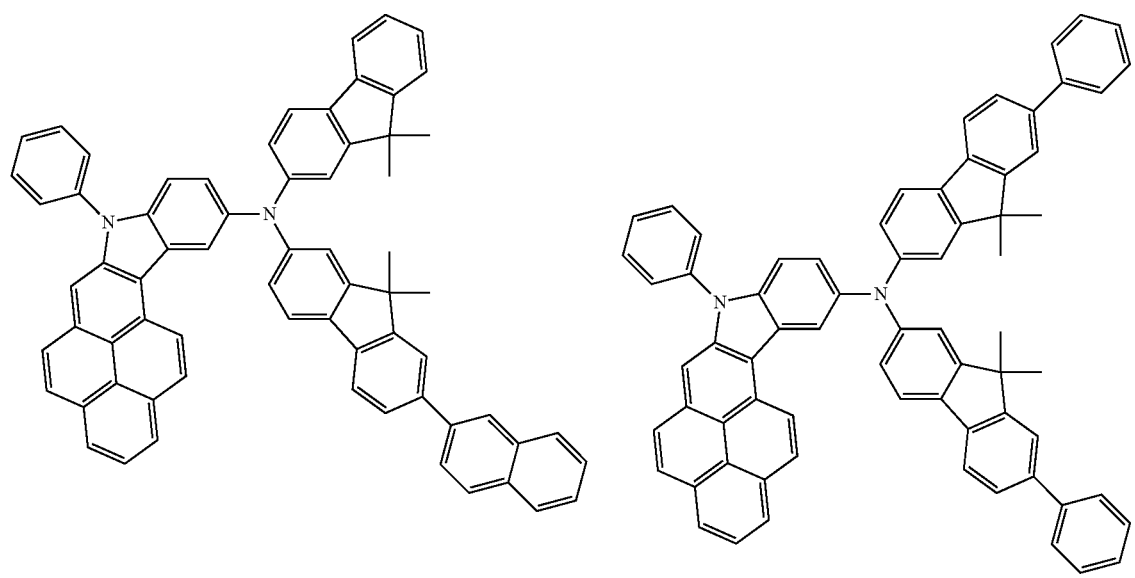

-continued
68
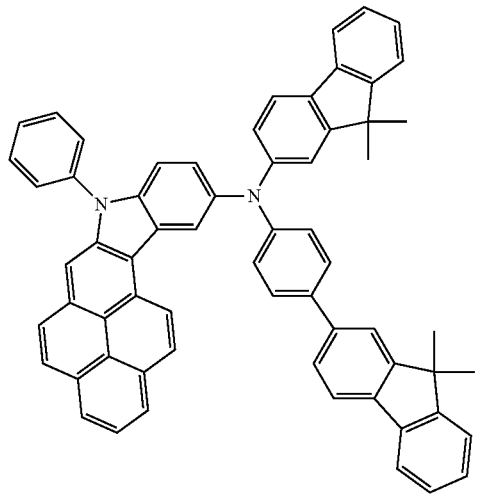
69
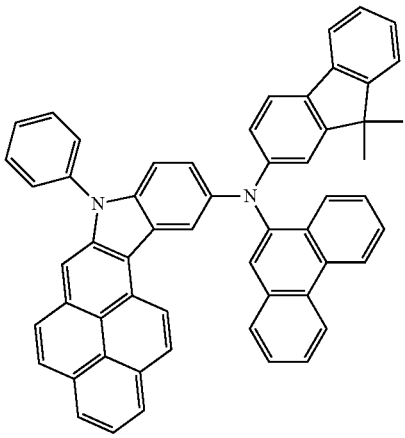
70
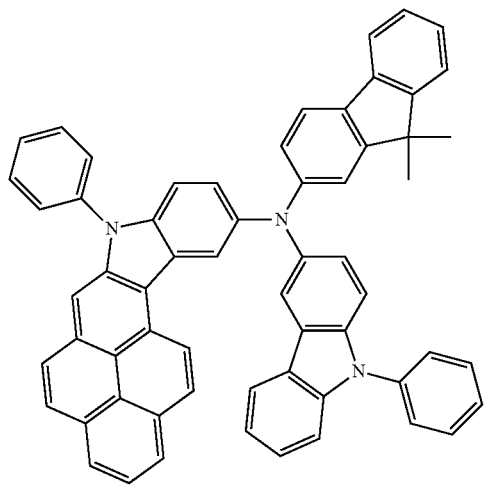
71
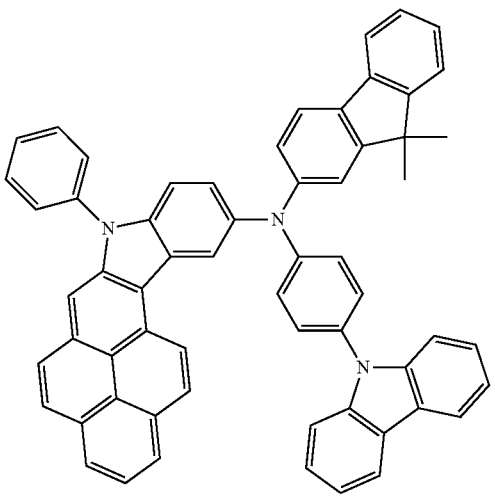
72
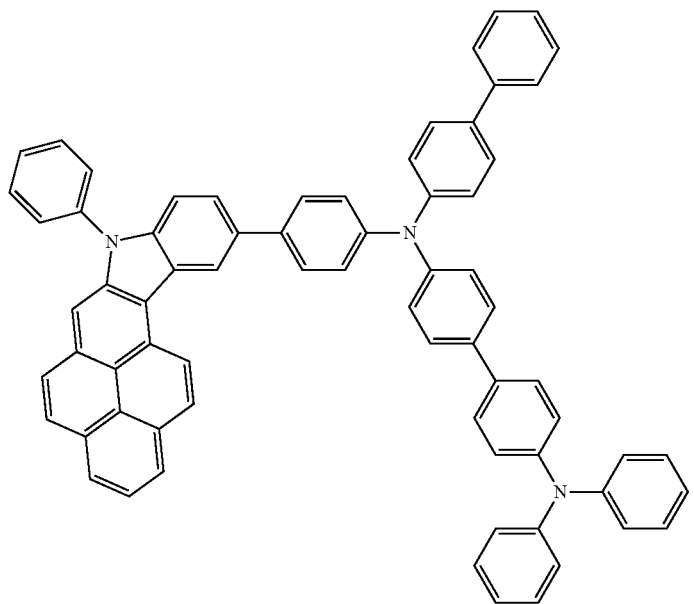

An organic light-emitting device according to an embodiment of the present invention includes a first electrode, a second electrode, and an organic layer between the first electrode and the second electrode, and the organic layer including the amine compound of Formula 1 described above.

The organic layer containing the amine compound of Formula 1 may include a hole injection layer, a hole transport layer, or a single layer having both hole injection and hole transport capabilities.

When the organic layer including the amine compound of Formula 1 is an emission layer, the amine compound of Formula 1 may be used as a host for a fluorescent host or phosphorescent device, or as a fluorescent dopant.

According to an embodiment, the organic layer of the organic light-emitting device may include an emitting layer, a hole transport layer, and a hole injection layer, and when the emitting layer, the hole transport layer, or the hole injection layer includes the compound of Formula 1, the emitting layer may include a known anthracene compound, a known arylamine compound, or a known styryl compound.

In the known anthracene compound, the known arylamine compound, or the known styryl compound, at least one hydrogen atom may be substituted with a substituent such as those described above in connection with the $C_1$-$C_{60}$ alkyl group.

The arylamine refers to an amino group substituted with the $C_1$-$C_{60}$ aryl group.

According to another embodiment, the organic layer of the organic light-emitting device may include an emitting layer, a hole transport layer, and a hole injection layer, and when the emitting layer, the hole transport layer, or the hole injection layer includes the compound of Formula 1, a red emission layer, a green emission layer, a blue emission layer, or a white emission layer may include a known phosphorescent compound.

Meanwhile, the first electrode may be an anode, and the second electrode may be a cathode, but the reverse is also possible.

For example, the organic light-emitting device may have a first electrode/hole injection layer/emitting layer/second electrode structure, a first electrode/hole injection layer/hole transport layer/emitting layer/electron transport layer/second electrode structure, or a first electrode/hole injection layer/ hole transport layer/emitting layer/electron transport layer/ electron injection layer/second electrode structure. Alternatively, the organic light-emitting device may have a first electrode/single layer having both hole injection and hole transport capabilities/emitting layer/electron transport layer/ second electrode structure, or a first electrode/single layer having both hole injection and hole transport capabilities/ emitting layer/electron transport layer/electron injection layer/second electrode structure.

According to some embodiments of the present invention, the organic light-emitting device may be either a top-emission organic light-emitting device or a bottom-emission organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device according to the present embodiment includes a substrate (not shown), a first electrode (anode), a hole injection layer (HIL), a hole transport layer (HTL), an emitting layer (EML), an electron transport layer (ETL), an electron injection layer (EIL), and a second electrode (cathode).

First, a first electrode material having a high work function may be deposited or sputtered on the substrate to form the first electrode. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using various methods, for example, by vacuum deposition, spin coating, casting, Langmuir-Blodgett (LB) deposition, or the like.

When the HIL is formed by vacuum deposition, the deposition conditions may vary according to a material that is used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, the coating conditions may include a coating speed of about 2000 rpm to about 5000 rpm, and a thermal treatment temperature of about 80° C. to about 200° C., wherein the thermal treatment serves to remove the solvent after coating.

The HIL may be formed of the amine compound of Formula 1 or any material that is commonly used to form a HIL. Examples of the material that is used to form the HIL include a phthalocyanine compound such as copper phthalocyanine, 4,4',4"-tris (3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS), but are not limited thereto.

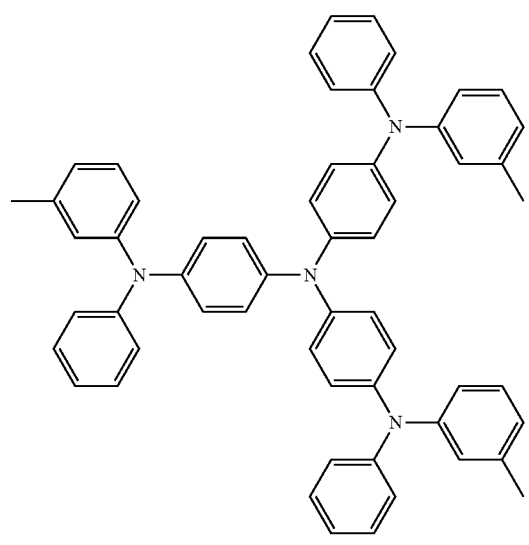

m-MTDATA

-continued

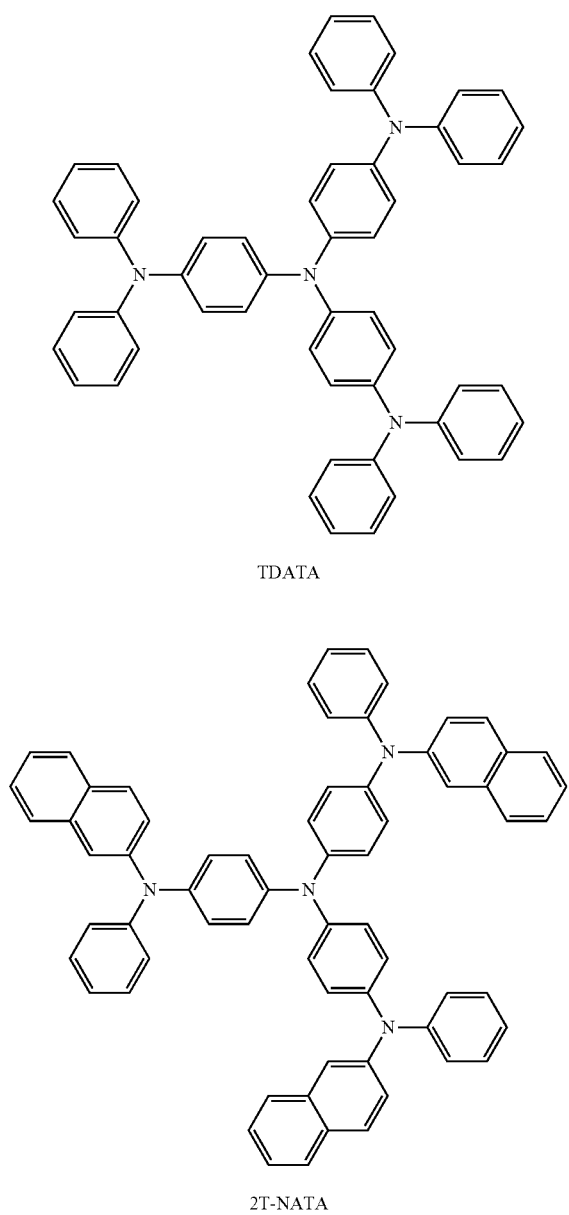

TDATA

2T-NATA

The HIL may have a thickness of about 100 Å to about 10000 Å, for example, a thickness of about 100 Å to about 1000 Å. When the thickness of the HIL is within these ranges, the HIL may have good hole injection characteristics without an increase in driving voltage.

Next, the HTL, may be formed on the HIL using various methods, for example, vacuum deposition, spin coating, casting, LB deposition, or the like. When the HTL is formed using vacuum deposition or spin coating, the deposition or coating conditions may be similar to those applied to form the HIL, though the deposition or coating conditions may vary according to the material that is used to form the HTL.

The HTL may be formed of the amine compound of Formula 1 or any known HTL material. Examples of such HTL materials include, but are not limited to, carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD), or the like. For example, TCTA may not only transport holes but also inhibit excitons from being diffused from the EML.

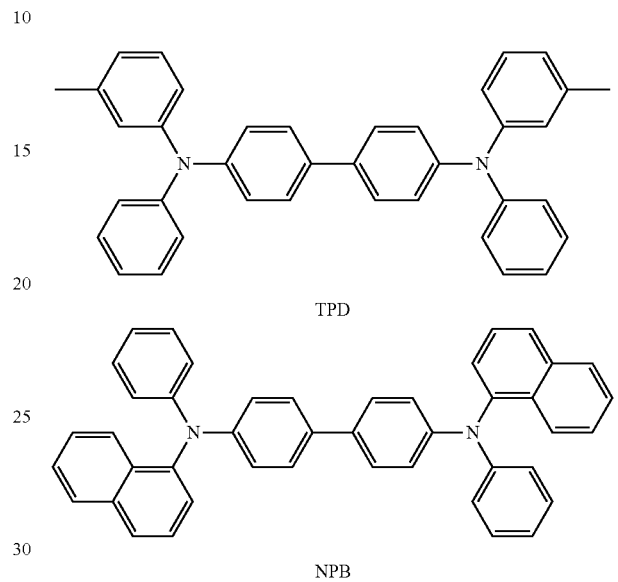

TPD

NPB

The HTL may have a thickness of about 50 Å to about 1000 Å, for example, a thickness of about 100 Å to about 600 Å. When the thickness of the HTL is within the above range, the HTL may have excellent hole transport characteristics without a substantial increase in driving voltage.

Next, the EML may be formed on the HTL using various methods, for example, by vacuum deposition, spin coating, casting, LB deposition, or the like. When the EML is formed by vacuum deposition or spin coating, the deposition or coating conditions may be similar to those used to form the HIL, though the deposition or coating conditions may vary according to the material that is used to form the EML.

The EML may include the amine compound represented by Formula 1 as previously described. For example, the amine compound of Formula 1 may be used as a host or a dopant. The EML may be formed using a variety of well-known light-emitting materials within discretion, and may also be formed using a well-known host and a well-known dopant. Dopants that may be used to form the EML may include either a fluorescent dopant or a phosphorescent dopant, which are widely known in the art.

Examples of the host include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), but are not limited thereto.

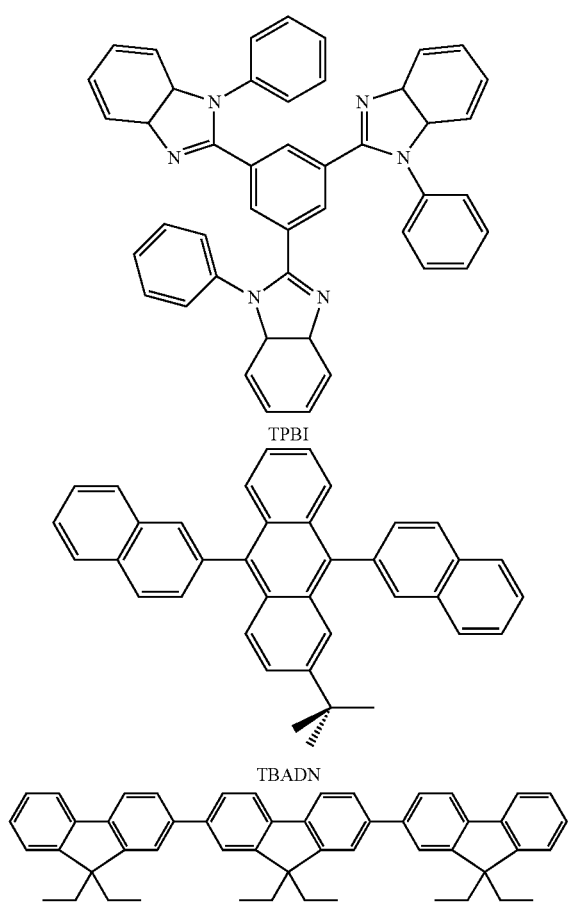
TPBI
TBADN
E3
PVK
Examples of red dopants include, but are not limited to, platinum(II) octaethylporphyrin (PtOEP), Ir(piq)$_3$, Btp$_2$Ir(acac), and DCJTB.
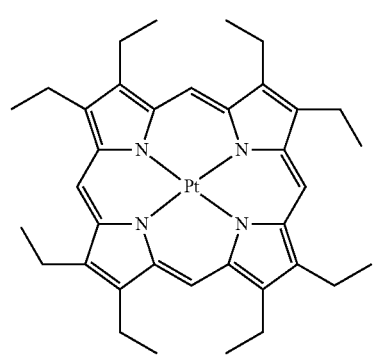
PtOEP
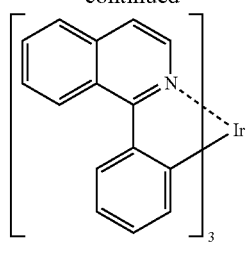
Ir(piq)$_3$
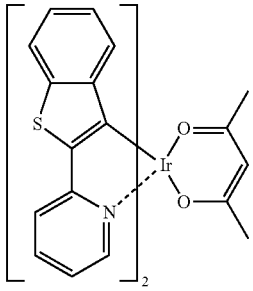
Btp$_2$Ir(acac)
Examples of green dopants may include, but are not limited to, Ir(ppy)$_3$ (where "ppy" denotes phenylpyridine), Ir(ppy)$_2$(acac), Ir(mpyp)$_3$, and C545T.
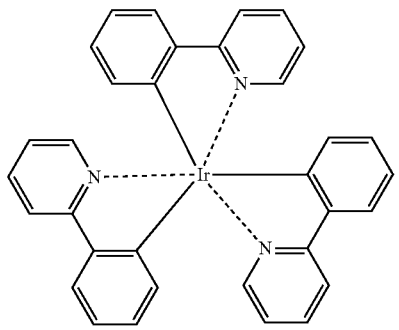
Ir(ppy)$_3$
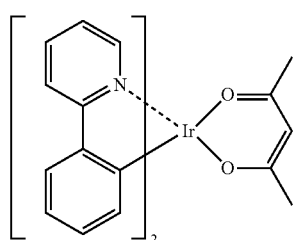
Ir(ppy)$_2$(acac)

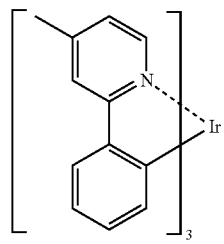
Ir(mpyp)₃
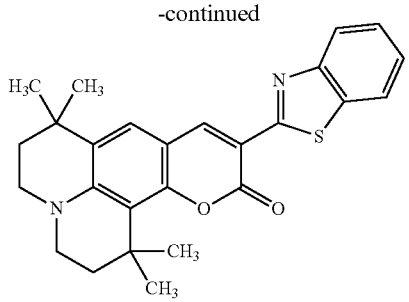
C545T
Examples of blue dopants include the amine compound of Formula 1, F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP), but are not limited thereto.
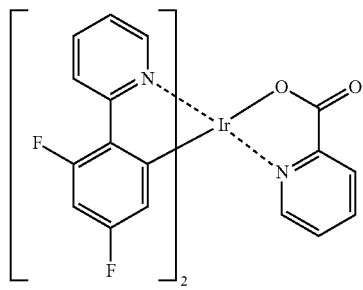
F₂Irpic
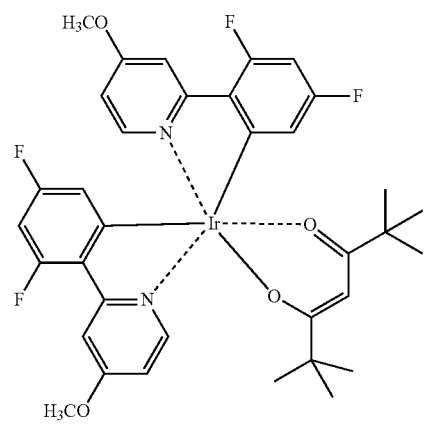
(F₂ppy)₂Ir(tmd)
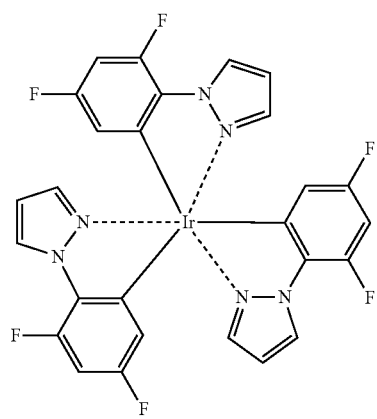
Ir(dfppz)₃

-continued

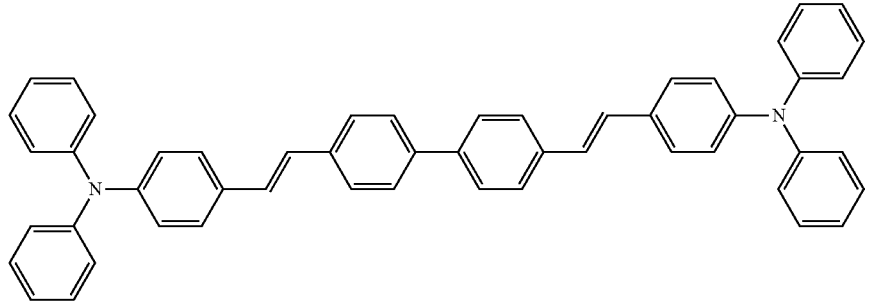

DPAVBi

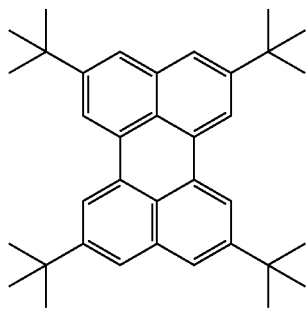

TBP

The amount of the dopant may be in the range of about 0.1 to about 20 parts by weight, or about 0.5 to about 12 parts by weight, based on 100 parts by weight of the EML material, which is equivalent to the total weight of the host and the dopant. When the amount of the dopant is within these ranges, concentration quenching may be substantially prevented.

The EML may have a thickness of about 100 Å to about 1,000 Å, for example, about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL, without limitation. Examples of such HBL materials include, but are not limited to, oxadiazole derivatives, triazole derivatives, phenathroline derivatives, Balq, and BCP.

The HBL may have a thickness of about 50 Å to about 1,000 Å, for example, about 100 Å to about 300 Å. When the thickness of the HBL is within these ranges, the HBL may have good hole blocking characteristics without a substantial increase in driving voltage.

Next, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL.

The ETL may be formed of any known materials used to form an ETL. Examples of known electron transporting materials include, but are not limited to, quinoline derivatives, such as tris(8-quinolinorate)aluminum (Alq3), TAZ, BAlq, or the like.

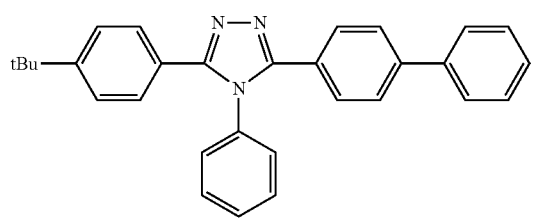

TAZ

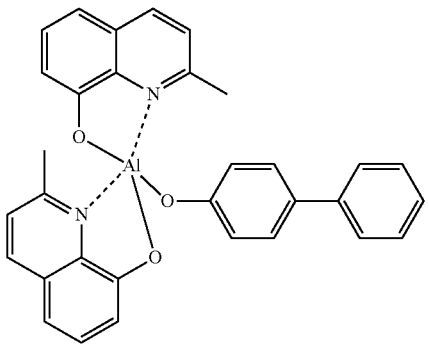

BAlq

The ETL may have a thickness of about 100 Å to about 1,000 Å, for example, about 100 Å to about 500 Å. When the thickness of the ETL is within these ranges, the ETL may have good electron transport characteristics without a substantial increase in driving voltage.

In addition, the EIL, which facilitates injection of electrons from the cathode, may be is formed on the ETL.

The EIL may be formed of LiF, NaCl, CsF, $Li_2O$, BaO, or the like, which is known in the art. The deposition or coating conditions may be similar to those applied to form the HIL, although the deposition and coating conditions may vary according to the material that is used to form the EIL.

The EIL, may have a thickness of about 1 Å to 100 Å, for example, about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may include a metal, an alloy, or an electrically conductive compound, which are materials having a low work function, or a mixture thereof. Examples of such materials include, but are not limited to, lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

The organic light-emitting device according to embodiments of the present invention may be included in various types of flat panel display devices, such as in a passive matrix organic light-emitting display device or in an active matrix organic light-emitting display device. When the organic light-emitting devices are included in an active matrix organic light-emitting display device including a thin-film transistor, the first electrode on the substrate may function as a pixel electrode and may be electrically connected to a source electrode or a drain electrode of the thin-film transistor. Moreover, the organic light-emitting devices may also be included in flat panel display devices having double-sided screens.

According to an embodiment, the organic light-emitting device may include a plurality of organic layers, wherein at least one of the organic layers may be formed by depositing the amine compound of Formula 1 or formed using a wet process including coating a solution of the amine compound of Formula 1.

Hereinafter, the present invention will be described in detail with reference to synthesis examples of Compounds 2, 20, 29, 32, 58, and 65 and other examples. However, these examples are for illustrative purposes only and are not intended to limit the scope of the present invention.

EXAMPLES

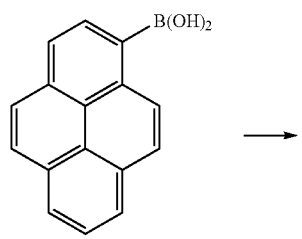

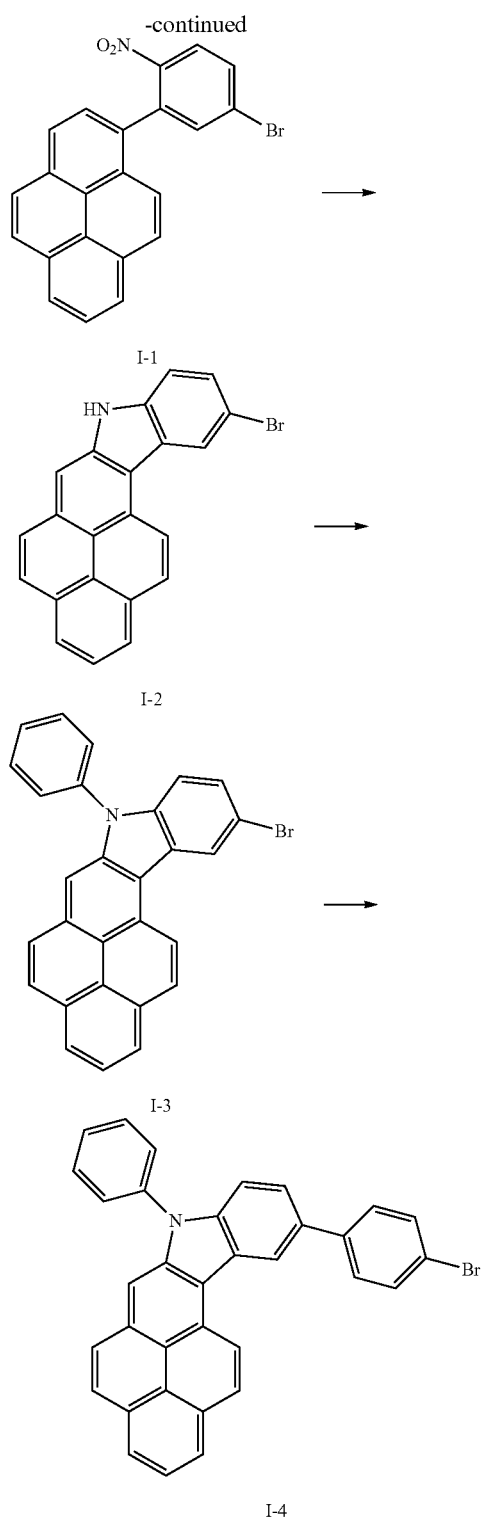

Synthesis Example 1

Synthesis of Intermediate I-1

4.93 g (20.0 mmol) of pyreneboronic acid, 5.62 g (20.0 mmol) of 2,4-dibromonitrobenzene, 1.15 g (1.0 mmol) of Pd(PPh$_3$)$_4$, and 8.29 g (60.0 mmol) of K$_2$CO$_3$ were dissolved in 60 ml of a THF/H$_2$O (2/1) mixed solution and the reaction mixture was stirred at a temperature of 70° C. for 5 hours. The reaction solution was cooled to room temperature and then 40 mL of water was added thereto and the resulting mixture was extracted three times using 50 mL of ethyl ether. An organic layer was collected and dried using magnesium sulfate to evaporate the solvent. The residue was separately purified using silica gel column chromatography to obtain 4.50 g (yield 56%) of Intermediate I-1. The obtained compound was identified by liquid chromatography/mass spectrometry (LC-MS) and nuclear magnetic resonance (NMR) spectroscopy. $C_{22}H_{12}BrNO_2$ cal.: 401.0. found 401.0

$^1$H NMR (CDCl$_3$, 400 MHz) δ (ppm) 8.28-8.26 (d, 1H), 8.15-8.03 (m, 7H), 8.01-7.97 (m, 2H), 7.74-7.71 (m, 1H), 7.53-7.50 (dd, 1H)

Synthesis Example 2

Synthesis of Intermediate I-2

4.02 g (10.0 mmol) of Intermediate I-1 and 5.77 g (22 mmol) of triphenylphosphine (PPh$_3$) were dissolved in 30 ml of 1,2-dichlorobenzene and the reaction mixture was stirred at a temperature of 170° C. for 12 hours. The reaction solution was cooled to room temperature and a solvent used was removed in a vacuum condition, and then the resulting reaction solution was extracted three times using 50 mL of water and 50 mL of dichloromethane. An organic layer was collected and dried using magnesium sulfate to evaporate the solvent. The residue was separately purified using silica gel column chromatography to obtain 2.78 g (yield 75%) of Intermediate I-2. The obtained compound was identified by LC-MS and NMR spectroscopy. $C_{22}H_{12}BrN$ cal.: 369.0. found 369.0

$^1$H NMR (CDCl$_3$, 400 MHz) δ (ppm) 9.65 (s, 1H), 9.14-9.12 (d, 1H), 8.84-8.82 (d, 1H), 8.43-8.41 (d, 1H), 8.18-8.16 (dd, 1H), 8.07-8.04 (m, 2H), 8.00-7.85 (m, 3H), 7.84-7.98 (dt, 1H), 7.36-7.32 (dd, 1H)

Synthesis Example 3

Synthesis of Intermediate I-3

3.70 g (10.0 mmol) of Intermediate I-2, 3.06 g (15.0 mmol) of iodobenzene, 0.19 g (1.0 mmol) of CuI, 0.05 g (0.2 mmol) of 18-Crown-6, and 4.15 g (30.0 mmol) of K$_2$CO$_3$ were dissolved in 30 ml of DMPU (1,3-Dimethyl-3,4,5,6-tetrahydro-2(1H)-pyrimidinone) and the reaction mixture was stirred at a temperature of 170° C. for 12 hours. The reaction solution was cooled to room temperature and extracted three times using 50 mL of water and 50 mL of dichloromethane. An organic layer was collected and dried using magnesium sulfate to evaporate the solvent. The residue was separately purified using silica gel column chromatography to obtain 4.06 g (yield 91%) of Intermediate I-3. The obtained compound was identified by LC-MS and NMR spectroscopy. $C_{28}H_{16}BrN$ cal.: 445.0. found 445.0

$^1$H NMR (CDCl$_3$, 400 MHz) δ (ppm) 9.14-9.11 (d, 1H), 8.90-8.87 (d, 1H), 8.38-8.35 (d, 1H), 8.15-8.11 (m, 2H), 8.01-7.96 (m, 2H), 7.90-7.86 (m, 2H), 7.51-7.45 (m, 5H), 7.37-7.30 (m, 1H), 8.19-7.14 (m, 1H)

Synthesis Example 4

Synthesis of Intermediate I-4

4.46 g (10.0 mmol) of Intermediate I-3, 3.01 g (15.0 mmol) of 4-bromophenylboronic acid, 0.58 g (0.5 mmol) of Pd(PPh$_3$)$_4$, and 4.15 g (30.0 mmol) of K$_2$CO$_3$ were dissolved in 30 ml of a THF/H$_2$O (2/1) mixed solution and the reaction mixture was stirred at a temperature of 70° C. for 5 hours. The reaction solution was cooled to room temperature and then 40 mL of water was added thereto and the resulting mixture was extracted three times using 50 mL of ethyl ether. An organic layer was collected and dried using magnesium sulfate to evaporate the solvent. The residue was separately purified using silica gel column chromatography to obtain 4.65 g (yield 89%) of Intermediate I-4. The obtained compound was identified by LC-MS and NMR spectroscopy. $C_{34}H_{20}BrN$ cal.: 521.1. found 521.1

$^1$H NMR (CDCl$_3$, 400 MHz) δ (ppm) 9.12-9.10 (d, 1H), 8.80-8.77 (d, 1H), 8.38-8.35 (dd, 1H), 8.16-8.13 (dd, 1H), 8.06 (s, 1H), 8.01-7.86 (m, 4H), 7.78-7.77 (dd, 1H), 7.53-7.46 (m, 4H), 7.39-7.32 (m, 1H), 7.31-7.28 (m, 2H), 7.11-7.08 (dt, 1H), 7.02-6.99 (dd, 2H)

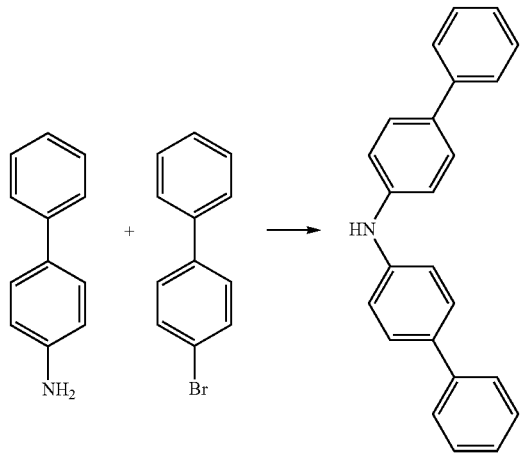

I-5

Synthesis Example 5

Synthesis of intermediate I-5

5.08 g (30.0 mmol) of 4-aminobiphenyl, 6.99 g (20.0 mmol) of 4-bromobiphenyl, 0.37 g (0.4 mmol) of Pd$_2$(dba)$_3$, 0.08 g (0.4 mmol) of PtBu$_3$, and 2.88 g (30.0 mmol) of KOtBu were dissolved in 60 ml of toluene and the reaction mixture was stirred at a temperature of 85° C. for 4 hours. The reaction solution was cooled to room temperature and then, 60 mL of water was added thereto and generated solid was separated by filtering and washed using dichloromethane, thereby preparing 5.93 g (yield 92%) of Intermediate I-5. The obtained compound was identified by LC-MS and NMR spectroscopy. $C_{24}H_{19}N$ cal.: 321.2. found 321.1

$^1$H NMR (CDCl$_3$, 400 MHz) δ (ppm) 7.61-7.54 (m, 8H), 7.40-7.30 (m, 6H), 7.11-6.90 (m, 4H), 5.51 (s, 1H)

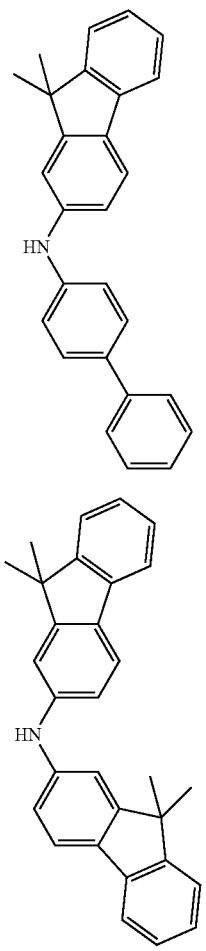

I-6

I-7

Synthesis Example 6

Synthesis of Intermediate I-6

The same synthesis method as the synthesis method for forming Intermediate compound I-5 was used using 2-amino-9,9-dimethyl fluorene instead of 4-aminobiphenyl. The reaction solution was cooled to room temperature and then 40 mL of water was added thereto and the resulting mixture was extracted three times using 50 mL of ethyl ether. An organic layer was collected and dried using magnesium sulfate to evaporate the solvent. The residue was separately purified using silica gel column chromatography to obtain 6.43 g of Intermediate I-6 (yield 89%). The obtained compound was identified by LC-MS and NMR spectroscopy. $C_{27}H_{23}N$ cal.: 361.2. found 361.2

$^1$H NMR (CDCl$_3$, 400 MHz) δ (ppm) 7.83-7.80 (d, 1H), 7.62-7.47 (m, 6H), 7.41-7.31 (m, 3H), 7.24-7.21 (dt, 1H), 7.13-7.11 (m, 1H), 9.99-6.93 (dt, 1H), 6.79-6.75 (h, 2H), 6.60-6.56 (dd, 1H), 5.44 (s, 1H), 1.67 (s, 6H)

Synthesis Example 7

Synthesis of Intermediate I-7

6.82 g (yield 85%) of Intermediate I-7 was obtained using 2-amino-9,9-dimethyl fluorene and 2-bromo-9,9-dimethyl fluorene in the same manner as in Synthesis Example 6 for forming Intermediate compound I-6. The obtained compound was identified by LC-MS and NMR spectroscopy. $C_{30}H_{27}N$ cal.: 401.2. found 401.2

$^1$H NMR (CDCl$_3$, 400 MHz) δ (ppm) 7.85-7.82 (dd, 1H), 7.54-7.50 (m, 4H), 7.28-7.23 (m, 2H), 7.21-7.19 (m, 2H), 7.11-6.93 (dt, 2H), 6.78-6.73 (dd, 2H), 5.36 (s, 1H), 1.65 (s, 12H)

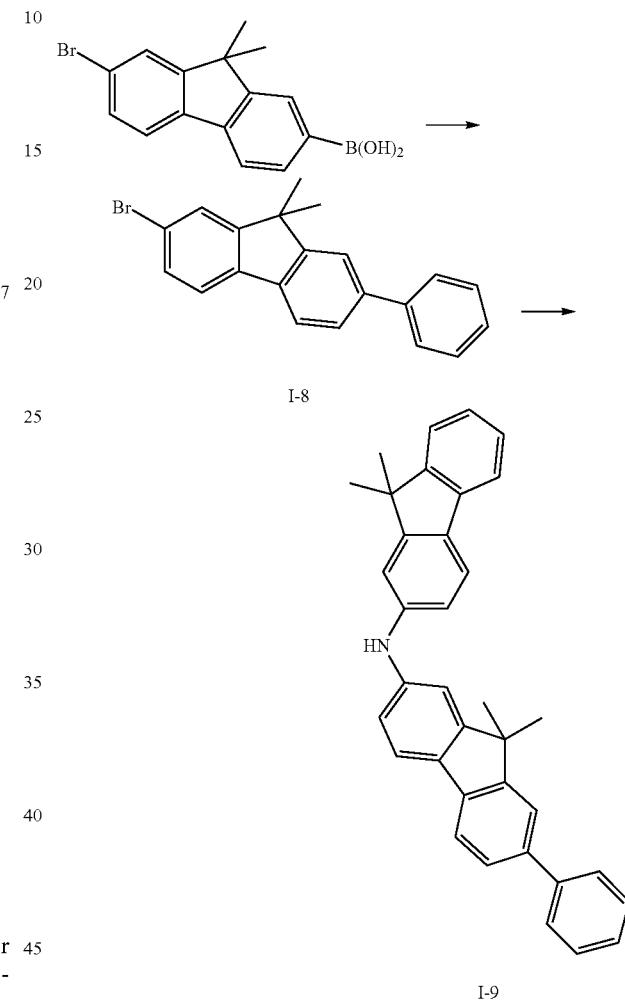

I-8

I-9

Synthesis Example 8

Synthesis of Intermediate I-8

6.34 g (20.0 mmol) of 2-bromo-9,9-dimethylfluorenyl-2'-boronic acid, 8.16 g (40.0 mmol) of iodobenzene, 1.15 g (1.0 mmol) of Pd(PPh$_3$)$_4$, and 8.29 g (60.0 mmol) of K$_2$CO$_3$ were dissolved in 80 ml of a THF/H$_2$O (2/1) mixed solution and the reaction mixture was stirred at a temperature of 70° C. for 5 hours. The reaction solution was cooled to room temperature and then 60 mL of water was added thereto and the resulting mixture was extracted three times using 60 mL of ethyl ether. An organic layer was collected and dried using magnesium sulfate to evaporate the solvent. The residue was separately purified using silica gel column chromatography to obtain 5.24 g (yield 75%) of Intermediate I-8. The obtained compound was identified by LC-MS and NMR spectroscopy. $C_{21}H_{17}Br$ cal.: 348.1. found 348.1

$^1$H NMR (CDCl$_3$, 400 MHz) δ (ppm) 7.69-7.67 (d, 1H), 7.56-7.52 (m, 2H), 7.50-7.46 (dd, 1H), 7.40-7.29 (m, 4H), 7.08-7.06 (d, 1H), 6.93-6.86 (m, 2H), 1.59 (s, 6H)

Synthesis Example 9

Synthesis of Intermediate I-9

4.21 g (yield 86%) of Intermediate I-9 was obtained using Intermediate I-8 and 2-amino-9,9-dimethyl fluorene in the same manner as in Synthesis Example 6 for forming Intermediate compound I-6. The obtained compound was identified by LC-MS and NMR spectroscopy. C$_{36}$H$_{31}$N cal.: 477.2. found 477.2

$^1$H NMR (CDCl$_3$, 400 MHz) δ (ppm) 7.86-7.84 (dd, 1H), 7.67-7.55 (m, 5H), 7.41-7.31-(m, 3H), 7.28-7.23 (dt, 1H), 7.13-7.06 (m, 3H), 7.01-6.97 (dt, 1H), 6.93-6.89 (m, 2H), 6.76-6.72 (dd, 2H), 5.34 (s, 1H), 1.69 (s, 6H), 1.68 (s, 6H)

I-3. The obtained compound was identified by LC-MS and NMR spectroscopy. C$_{34}$H$_{20}$BrN cal.: 521.1. found 521.1

$^1$H NMR (CDCl$_3$, 400 MHz) δ (ppm) 9.14-9.12 (d, 1H), 8.91-8.88 (d, 1H), 8.40-8.36 (dd, 1H), 8.16-8.13 (m, 2H), 8.04-7.98 (m, 2H), 7.94-7.88 (m, 2H), 7.62-7.58 (m, 2H), 7.57-7.54 (d, 1H), 7.42-7.32 (m, 5H), 7.28-7.24 (dd, 1H), 6.83-6.76 (m, 2H)

Synthesis Example 11

Synthesis of Intermediate I-11

5.03 g (yield 84%) of Intermediate I-11 was obtained using Intermediate I-10 in the same manner as in Synthesis Example 4 for forming Intermediate compound I-4. The obtained compound was identified by LC-MS and NMR spectroscopy. C$_{40}$H$_{24}$BrN cal.: 597.1. found 597.1

$^1$H NMR (CDCl$_3$, 400 MHz) δ (ppm) 9.24-9.22 (d, 1H), 8.80-8.77 (d, 1H), 8.38-8.36 (d, 1H), 8.16-8.143 (d, 1H), 8.08 (d, 1H), 8.01-7.86 (m, 4H), 7.78-7.77 (dd, 1H), 7.61-7.59 (dd, 2H), 7.45-7.39 (m, 2H), 7.38-7.28 (m, 5H), 7.13-7.09 (dd, 1H), 7.01-6.97 (m, 2H), 6.78-6.69 (m, 2H)

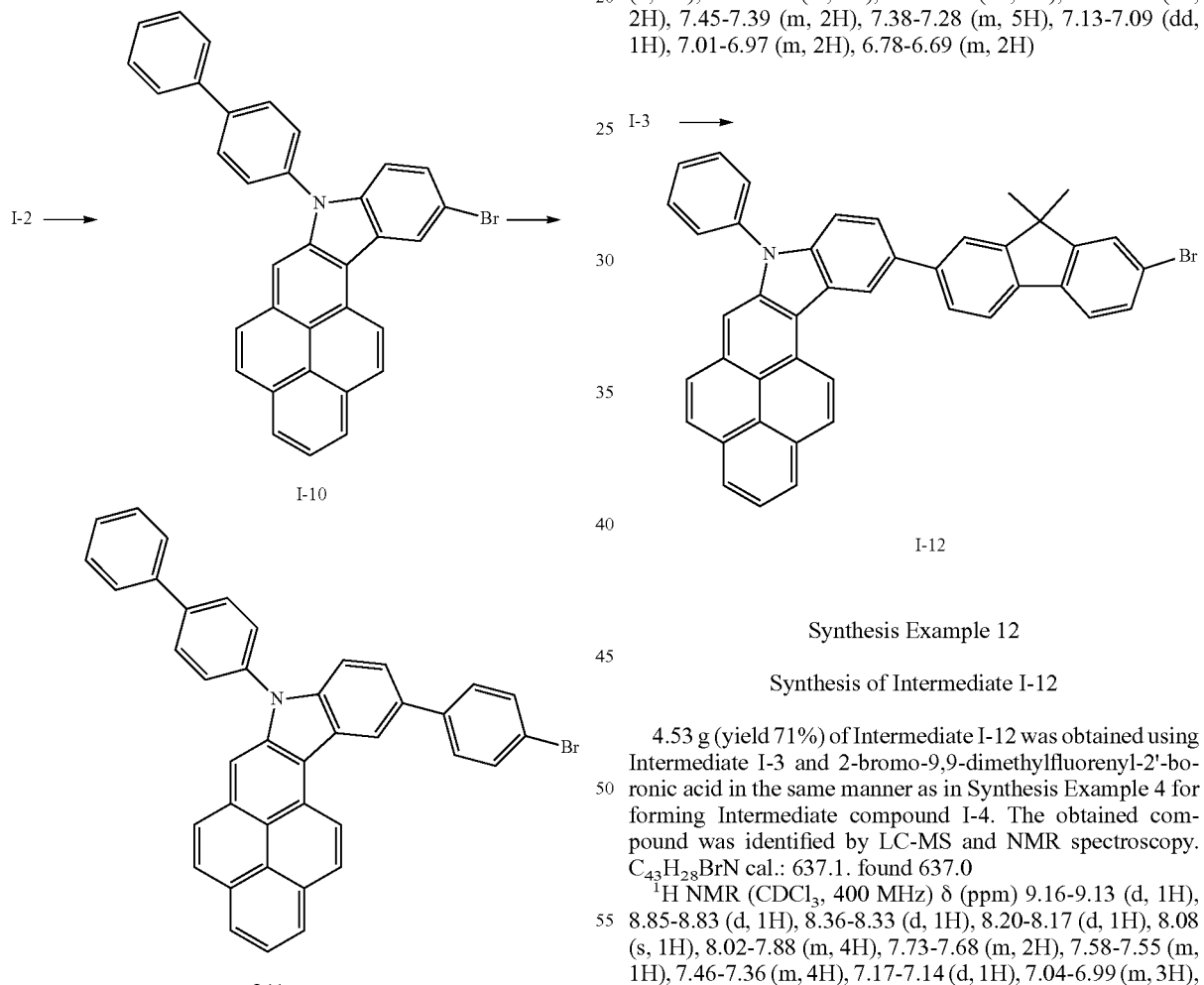

Synthesis Example 10

Synthesis of Intermediate I-10

4.28 g (yield 82%) of Intermediate I-10 was obtained using Intermediate I-2 and 4-bromobiphenyl in the same manner as in Synthesis Example 3 for forming Intermediate compound Synthesis Example 12

Synthesis of Intermediate I-12

4.53 g (yield 71%) of Intermediate I-12 was obtained using Intermediate I-3 and 2-bromo-9,9-dimethylfluorenyl-2'-boronic acid in the same manner as in Synthesis Example 4 for forming Intermediate compound I-4. The obtained compound was identified by LC-MS and NMR spectroscopy. C$_{43}$H$_{28}$BrN cal.: 637.1. found 637.0

$^1$H NMR (CDCl$_3$, 400 MHz) δ (ppm) 9.16-9.13 (d, 1H), 8.85-8.83 (d, 1H), 8.36-8.33 (d, 1H), 8.20-8.17 (d, 1H), 8.08 (s, 1H), 8.02-7.88 (m, 4H), 7.73-7.68 (m, 2H), 7.58-7.55 (m, 1H), 7.46-7.36 (m, 4H), 7.17-7.14 (d, 1H), 7.04-6.99 (m, 3H), 6.87 (6.83 (m, 2H), 1.64 (s, 6H)

Synthesis Example 13

Synthesis of Compound 2

5.22 g (10.0 mmol) of Intermediate I-4, 3.21 g (10.0 mmol) of Intermediate I-5, 0.19 g (0.2 mmol) of Pd$_2$(dba)$_3$, 0.04 g (0.2 mmol) of PtBu$_3$, and 1.44 g (15.0 mmol) of KOtBu were dissolved in 30 ml of toluene and the reaction mixture was stirred at a temperature of 85° C. for 4 hours. The reaction solution was cooled to room temperature and then 40 mL of water was added thereto and the resulting mixture was extracted three times using 40 mL of ethyl ether. An organic layer was collected and dried using magnesium sulfate to evaporate the solvent. The residue was separately purified using silica gel column chromatography to obtain 5.57 g (yield 73%) of Compound 2. The obtained compound was identified by HR-MS and NMR spectroscopy. $C_{58}H_{38}N_2$ cal.: 762.3035. found [M+1] 763.3029

$^1$H NMR (CDCl$_3$, 400 MHz) δ (ppm) 9.14-9.12 (d, 1H), 8.82-8.79 (d, 1H), 8.38-8.35 (d, 1H), 8.15-8.12 (d, 1H), 8.07 (s, 1H), 8.00-7.86 (m, 5H), 7.78-7.64 (m, 10H), 7.51-7.46 (m, 4H), 7.43-7.29 (m, 7H), 7.22-7.19 (dd, 1H), 6.68-6.62 (m, 6H)

Synthesis Example 14

Synthesis of Compound 20

6.10 g (yield 76%) of Compound 20 was obtained using Intermediate I-4 and Intermediate I-6 in the same manner as in Synthesis Example 13 for forming Compound 2. The obtained compound was identified by HR-MS and NMR spectroscopy. $C_{61}H_{42}N_2$ cal.: 802.3348. found [M+1] 803.3342

$^1$H NMR (CDCl$_3$, 400 MHz) δ (ppm) 9.10-9.07 (d, 1H), 8.76-8.75 (d, 1H), 8.41-8.38 (d, 1H), 8.16-8.13 (d, 1H), 8.05 (s, 1H), 8.02-7.83 (m, 6H), 7.72-7.66 (m, 6H), 7.59-7.56 (dd, 1H), 7.48-7.44 (m, 4H), 7.41-7.28 (m, 5H), 7.25-7.14 (m, 3H), 7.03-6.97 (dt, 1H), 6.74-6.67 (m, 4H), 6.59-6.56 (dd, 1H), 1.59 (s, 6H)

Synthesis Example 15

Synthesis of Compound 29

6.33 g (yield 72%) of Compound 29 was obtained using Intermediate I-11 and Intermediate I-6 in the same manner as in Synthesis Example 13 for forming Compound 2. The obtained compound was identified by HR-MS and NMR spectroscopy. $C_{67}H_{46}N_2$ cal.: 878.3661. found [M+1] 879.3655

$^1$H NMR (CDCl$_3$, 400 MHz) δ (ppm) 9.16-9.13 (d, 1H), 8.79-8.76 (d, 1H), 8.39-8.37 (d, 1H), 8.22-8.19 (dd, 1H), 8.10 (s, 1H), 7.99-7.83 (m, 6H), 7.77-7.64 (m, 7H), 7.59-7.55 (m, 3H), 7.42-7.37 (m, 4H), 7.33-7.29 (m, 3H), 7.23-7.13 (m, 4H), 7.05-6.99 (dt, 1H), 6.83-6.79 (m, 2H), 6.63-6.60 (m, 4H), 6.54-6.51 (dd, 1H), 1.61 (s, 6H)

Synthesis Example 16

Synthesis of Compound 32

6.06 g (yield 69%) of Compound 32 was obtained using Intermediate I-12 and Intermediate I-5 in the same manner as in Synthesis Example 13 for forming Compound 2. The obtained compound was identified by HR-MS and NMR spectroscopy. $C_{67}H_{46}N_2$ cal.: 878.3661. found [M+1] 879.3656

$^1$H NMR (CDCl$_3$, 400 MHz) δ (ppm) 9.06-9.03 (d, 1H), 8.61-8.59 (d, 1H), 8.28-8.25 (d, 1H), 8.07-8.03 (d, 1H), 7.98-7.83 (m, 5H), 7.79-7.76 (m, 4H), 7.68-7.64 (m, 5H), 7.56-7.46 (m, 5H), 7.40-7.31 (m, 7H), 7.27-7.24 (dd, 1H), 7.17-7.13 (dd, 2H), 7.03-6.98 (dt, 2H), 6.75-6.72 (m, 4H), 6.63-6.59 (m, 1H), 1.55 (s, 6H)

Synthesis Example 17

Synthesis of Compound 58

6.49 g (yield 77%) of Compound 58 was obtained using Intermediate I-4 and Intermediate I-7 in the same manner as in Synthesis Example 13 for forming Compound 2. The obtained compound was identified by HR-MS and NMR spectroscopy. $C_{64}H_{46}N_2$ cal.: 842.3661. found [M+1] 843.3657

$^1$H NMR (CDCl$_3$, 400 MHz) δ (ppm) 9.09-9.05 (d, 1H) 8.67-8.65 (dd, 1H), 8.53-8.50 (d, 1H) 8.01-7.99 (d, 1H), 7.94 (s, 1H), 7.86-7.75 (m, 5H), 7.66-7.62 (m, 2H), 7.58-7.54 (m, 3H), 7.46-7.43 (dd, 3H), 7.38-7.33 (m, 4H), 7.27-7.21 (m, 1H), 7.16-7.11 (m, 3H), 7.08-7.07 (m, 2H), 6.94-6.89 (dt, 2H), 6.62-6.59 (m, 2H), 6.42-6.40 (m, 2H), 1.66 (s, 12H)

Synthesis Example 18

Synthesis of Compound 65

5.48 g (yield 65%) of Compound 65 was obtained using Intermediate I-3 and Intermediate I-9 in the same manner as in Synthesis Example 13 for forming Compound 2. The obtained compound was identified by HR-MS and NMR spectroscopy. $C_{64}H_{46}N_2$ cal.: 842.3661. found [M+1] 843.3653

$^1$H NMR (CDCl$_3$, 400 MHz) δ (ppm) 9.18-9.16 (d, 1H), 8.99-8.97 (d, 1H), 8.47-8.45 (d, 1H), 8.23 (s, 1H), 8.14-8.12 (d, 1H), 8.00-7.96 (dt, 3H), 7.90-7.85 (dt, 2H), 7.69-7.67 (dd, 1H), 7.59-7.51 (m, 4H), 7.49-7.44 (m, 5H), 7.44-7.29 (m, 5H), 7.24-7.07 (m, 4H), 7.02-7.01 (d, 1H), 6.99-6.87 (m, 2H), 6.61-6.57 (dd, 2H), 1.63 (s, 6H), 1.62 (s, 6H)

Example 1

To manufacture an anode, a Corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, first, 2T-NATA, which is a known HIL material, was vacuum-deposited on the glass substrate to form a HIL having a thickness of 600 Å. Then, Compound 2 as a hole transport compound was vacuum deposited on the HIL to form a HTL having a thickness of 300 Å.

Then, a green fluorescent host (Alq3) and a green fluorescent dopant (C545T) were simultaneously deposited in a weight ratio of 98:2 on the HTL, to form an EML having a thickness of about 300 Å.

Then, Alq3 was deposited on the EML to form an ETL having a thickness of 300 Å, and then LiF, which is a halogenated alkali metal, was deposited on the ETL to form an EIL in having a thickness of 10 Å, and Al was vacuum-deposited on the EIL, to form a cathode having a thickness of 3000 Å, thereby forming an LiF/Al electrode. As a result, an organic light-emitting device was completely manufactured.

The organic light-emitting device had a driving voltage of 6.35 V at a current density of 50 mA/cm$^2$, a high luminosity of 7943 cd/m$^2$, color coordinates of (0.310, 0.643), a luminescent efficiency of 15.89 cd/A, and a half-lifespan of 493 hours at 100 mA/cm$^2$.

Example 2

An organic light-emitting device was manufactured in the same manner as in Example 1, except that the hole transport layer was formed using Compound 20 instead of Compound 2.

The organic light-emitting device had a driving voltage of 6.38 V at a current density of 50 mA/cm$^2$, a high luminosity of 8,196 cd/m$^2$, color coordinates of (0.309, 0.643), a luminescent efficiency of 16.39 cd/A, and a half-lifespan of 532 hours at 100 mA/cm$^2$.

Example 3

An organic light-emitting device was manufactured in the same manner as in Example 1, except that the hole transport layer was formed using Compound 29 instead of Compound 2.

The organic light-emitting device had a driving voltage of 6.32 V at a current density of 50 mA/cm$^2$, a high luminosity of 8,230 cd/m$^2$, color coordinates of (0.310, 0.642), a luminescent efficiency of 16.46 cd/A, and a half-lifespan of 511 hours at 100 mA/cm$^2$.

Example 4

An organic light-emitting device was manufactured in the same manner as in Example 1, except that the hole transport layer was formed using Compound 32 instead of Compound 2.

The organic light-emitting device had a driving voltage of 6.12 V at a current density of 50 mA/cm$^2$, a high luminosity of 8,540 cd/m$^2$, color coordinates of (0.308, 0.642), a luminescent efficiency of 17.08 cd/A, and a half-lifespan of 489 hours at 100 mA/cm$^2$.

Example 5

An organic light-emitting device was manufactured in the same manner as in Example 1, except that the hole transport layer was formed using Compound 58 instead of Compound 2.

The organic light-emitting device had a driving voltage of 6.34 V at a current density of 50 mA/cm$^2$, a high luminosity of 8,046 cd/m$^2$, color coordinates of (0.310, 0.641), a luminescent efficiency of 16.09 cd/A, and a half-lifespan of 496 hours at 100 mA/cm$^2$.

Example 6

An organic light-emitting device was manufactured in the same manner as in Example 1, except that the hole transport layer was formed using Compound 65 instead of Compound 2.

The organic light-emitting device had a driving voltage of 6.45 V at a current density of 50 mA/cm$^2$, a high luminosity of 7,980 cd/m$^2$, color coordinates of (0.311, 0.644), a luminescent efficiency of 15.96 cd/A, and a half-lifespan of 480 hours at 100 mA/cm$^2$.

Comparative Example 1

An organic light-emitting device was manufactured in the same manner as in Example 1, except that the hole transport layer was formed using 4,4'-bis[N-(1-naphthyl)-N-phenylamino]biphenyl (hereinafter, NPB), which is a known material.

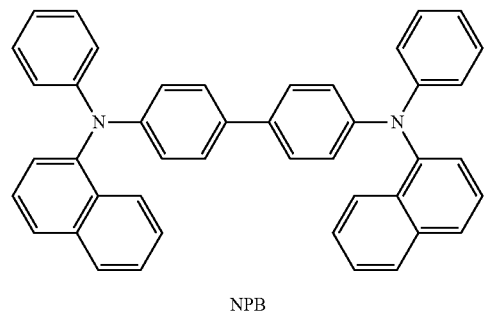 [SMILES: c1ccc(N(c2ccc(-c3ccc(N(c4ccccc4)c4cccc5ccccc45)cc3)cc2)c2cccc3ccccc23)cc1 ; "NPB"]

NPB

The organic light-emitting device had a driving voltage of 7.45V, a luminosity of 6,102 cd/m$^2$, color coordinates of (0.309, 0.642), which are similar to the results of the organic light-emitting devices manufactured according to Examples 1 through 6, a luminescent efficiency of 12.2 cd/A, and a half lifespan of 237 hours.

The organic light-emitting devices manufactured using the amine compounds represented by Formula 1 according to embodiments showed improvement in driving voltage and I-V-L characteristics, as compared to those manufactured using NPB. In particular, lifetime was markedly improved. Characteristics of the organic light-emitting devices manufactured according to Examples 1 through 6 and Comparative Example 1 are shown in Table 1.

TABLE 1

| | Hole transport material | Driving voltage (V) | Current Density (mA/cm$^2$) | Luminance (cd/m$^2$) | Efficiency (cd/A) | Half life-span (hr 100 mA/cm$^2$) |
|---|---|---|---|---|---|---|
| Example 1 | Compound 2 | 6.35 | 50 | 7943 | 15.89 | 493 hr |
| Example 2 | Compound 20 | 6.38 | 50 | 8196 | 16.39 | 532 hr |
| Example 3 | Compound 29 | 6.32 | 50 | 8230 | 16.46 | 511 hr |
| Example 4 | Compound 32 | 6.12 | 50 | 8540 | 17.08 | 489 hr |
| Example 5 | Compound 58 | 6.34 | 50 | 8046 | 16.09 | 496 hr |
| Example 6 | Compound 65 | 6.45 | 50 | 7980 | 15.96 | 480 hr |
| Comparative Example 1 | NPB | 7.45 | 50 | 6102 | 12.2 | 237 hr |

As described above, novel amine compounds according to the one or more of the above embodiments of the present invention have good electrical characteristics, good charge transporting capabilities, and good emission characteristics, and may be used to prevent crystallization due to high glass transition temperatures ($T_g$). The amine compounds may also be used as electron transporting materials for most color-fluorescent and phosphorescent devices, such as red, green, blue, and white fluorescent and phosphorescent devices, or as red, green, blue or white-light emitting materials. Thus, an organic light-emitting device with high-efficiency, low-driving voltage, high luminance, and long lifespan may be manufactured using the amine compounds.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An amine compound represented by Formula 1 below;

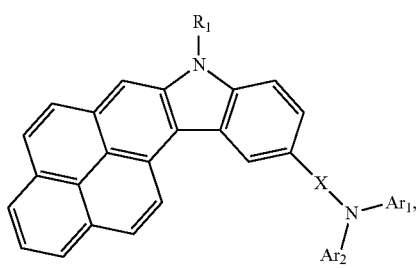

Formula 1 wherein
$R_1$ is selected from the group consisting of a substituted or unsubstituted C1 to C60 alkyl group, a substituted or unsubstituted C3 to C60 cycloalkyl group, a substituted or unsubstituted C1 to C60 alkoxy group, a substituted or unsubstituted C5 to C60 aryloxy group, a substituted or unsubstituted C5 to C60 arylthio group, a substituted or unsubstituted C5 to C60 aryl group, a substituted or unsubstituted C3 to C60 heteroaryl group, and a substituted or unsubstituted C6 to C60 condensed polycyclic group, $Ar_1$ and $Ar_2$ are each independently one selected from the group consisting of a substituted or unsubstituted C3 to C60 cycloalkyl group, a substituted or unsubstituted C5 to C60 aryloxy group, a substituted or unsubstituted C5 to C60 arylthio group, a substituted or unsubstituted C5 to C60 aryl group, a substituted or unsubstituted C3 to C60 heteroaryl group, and a substituted or unsubstituted C6 to C60 condensed polycyclic group, $Ar_1$ and $Ar_2$ can optionally be linked to each other to form an aromatic ring, and X is a divalent linking group represented by —$(Ar_3)_n$— where $Ar_3$ is one selected from the group consisting of a substituted or unsubstituted C5 to C60 arylene group, a substituted or unsubstituted C3 to C60 heteroarylene group, and a substituted or unsubstituted C6 to C60 condensed polycyclic group, n is an integer in the range of 1 through 10, the "n" groups of $Ar_3$ are identical to or different from each other, and among n groups of $Ar_3$, two or more neighboring $Ar_3$ groups are fused with each other or linked to each other by a single bond.

2. The amine compound of claim 1, wherein in Formula 1, $R_1$ is selected from the group consisting of a substituted or unsubstituted C5 to C20 aryl group and a substituted or unsubstituted C6 to C20 condensed polycyclic group.

3. The amine compound of claim 1, wherein in Formula 1, $R_1$ is selected from the group consisting of a C1 to C20 alkyl group, and Formulae 2a and 2b below:

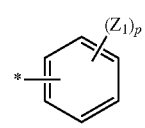

Formula 2a

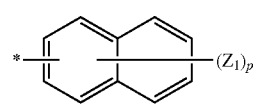

Formula 2b in Formulae 2a and 2b,
$Z_1$ is selected from the group consisting of a hydrogen atom, heavy hydrogen, a C1 to C20 alkyl group, a C5 to C20 substituted or unsubstituted aryl group, a C3 to C20 substituted or unsubstituted heteroaryl group, a C6 to C20 substituted or unsubstituted condensed polycyclic group, a halogen atom, a cyano group, a nitro group, a hydroxyl group, and a carboxyl group;

p is an integer in the range of 1 through 8; and

"*" represents a bond.

4. The amine compound of claim 1, wherein in Formula 1, $R_1$ is selected from the group consisting of a methyl group, an ethyl group, a propyl group, a butyl group, a pentyl group, and Formulae 3a through 3c below:

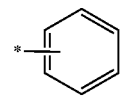

Formula 3a

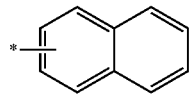

Formula 3b

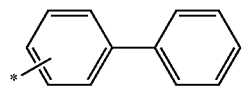

Formula 3c in Formulae 3a through 3c, "*" represents a bond.

5. The amine compound of claim 1, wherein in Formula 1, $Ar_1$ and $Ar_2$ are each independently selected from the group consisting of a substituted or unsubstituted C5 to C20 aryl group, and a substituted or unsubstituted C3 to C20 heteroaryl group.

6. The amine compound of claim 1, wherein in Formula 1, $Ar_1$ or $Ar_2$ is selected from the group consisting of Formulae 4a through 4d:

Formula 4a

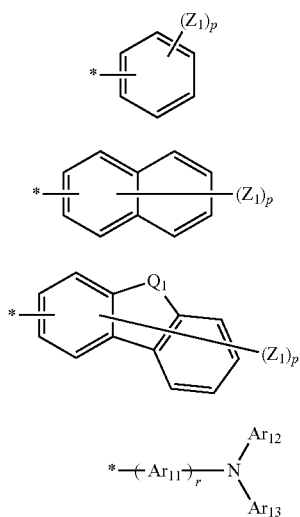

Formula 4b

Formula 4c

Formula 4d in Formulae 4a through 4d, $Q_1$ is selected from the group consisting of linking groups represented by —C($R_2$)($R_3$)— and —N($R_2$)—;

$Z_1$, $Ar_{12}$, $Ar_{13}$, $R_2$, and $R_3$ are each independently selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a halogen atom, a cyano group, a nitro group, a hydroxyl group, and a carboxyl group;

$Ar_{11}$ is selected from the group consisting of a substituted or unsubstituted C5 to C20 arylene group, and a substituted or unsubstituted C3 to C20 heteroarylene group;

p is an integer in the range of 1 through 8;

r is an integer in the range of 1 through 5; and

"*" represents a bond.

7. The amine compound of claim 1, wherein in Formula 1, $Ar_1$ or $Ar_2$ is selected from the group consisting of Formulae 5a through 5f below:

Formula 5a

Formula 5b

Formula 5c

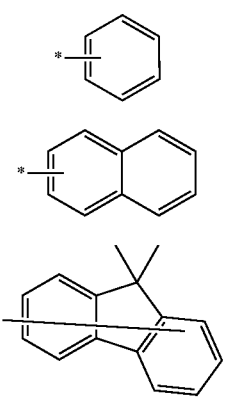

-continued

Formula 5d

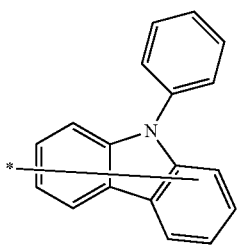

Formula 5e

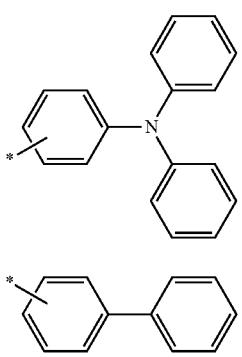

Formula 5f in Formulae 5a through 5f, "*" represents a bond.

8. The amine compound of claim 1, wherein $Ar_3$ is selected from the group consisting of a substituted or unsubstituted C5 to C20 arylene group, a substituted or unsubstituted C3 to C20 heteroarylene group, and a substituted or unsubstituted C6 to C20 condensed polycyclic group.

9. The amine compound of claim 1, wherein $Ar_3$ is selected from the group consisting of Formulae 6a through 6e:

Formula 6a

Formula 6b

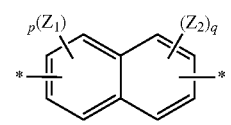

Formula 6c

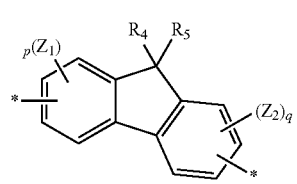

Formula 6d

-continued

Formula 6e

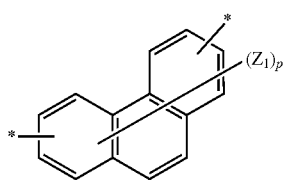

in Formulae 6a through 6e,
$Y_1$ is selected from the group consisting of linking groups represented by —S— and —O—;
$Z_1, Z_2, R_4,$ and $R_5$ are each independently selected from the group consisting of a hydrogen atom, heavy hydrogen, a C1 to C20 alkyl group, a substituted or unsubstituted C5 to C20 aryl group, a substituted or unsubstituted C3 to C20 heteroaryl group, a substituted or unsubstituted C6 to C20 condensed polycyclic group, a halogen atom, a cyano group, a nitro group, a hydroxyl group, and a carboxyl group;
p is an integer in the range of 1 through 10;
q is an integer in the range of 1 through 8; and
"*" represents a bond.

10. The amine compound of claim 1, wherein n is 1.
11. The amine compound of claim 1, wherein in Formula 1, X is selected from the group consisting of Formulae 7a through 7g below:

Formula 7a

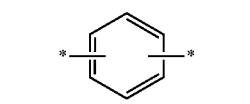

Formula 7b

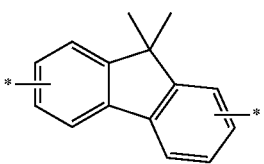

Formula 7c

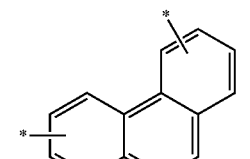

Formula 7d

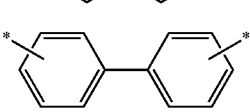

Formula 7e

Formula 7f

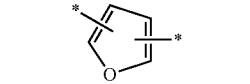

Formula 7g

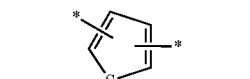

in Formulae 7a through 7g, "*" represents a bond.

12. The amine compound of claim 1, wherein in Formula 1,
$R_1$ is selected from the group consisting of a methyl group, an ethyl group, a propyl group, a butyl group, a pentyl group, and Formulas 3a through 3c below:

Formula 3a

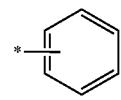

Formula 3b

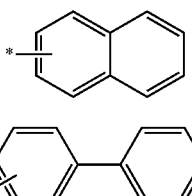

Formula 3c

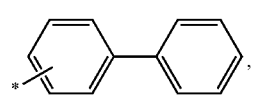

$Ar_1$ or $Ar_2$ is selected from the group consisting of Formulae 5a through 5f below:

Formula 5a

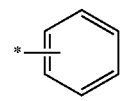

Formula 5b

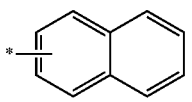

Formula 5c

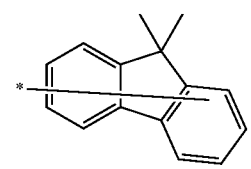

Formula 5d

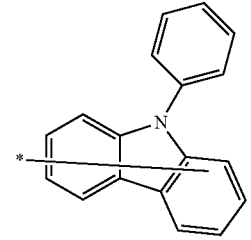

Formula 5e

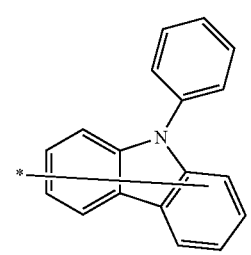

Formula 5f

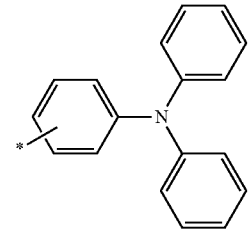

X is selected from the group consisting of Formulae 7a through 7g:

Formula 7a
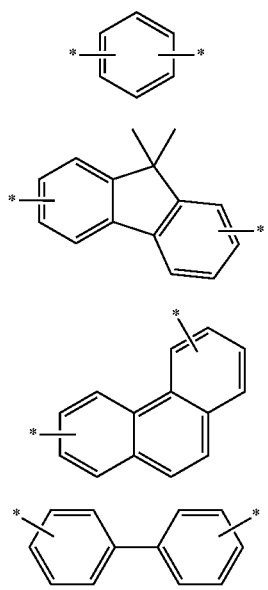
Formula 7b
Formula 7c
Formula 7d
Formula 7e
Formula 7f
Formula 7g
and in Formulas 3a through 3c, 5a through 5f, and 7a through 7g, "*" represents a bond.
13. The amine compound of claim 1 wherein the compound of Formula 1 is selected from the group consisting of compounds having the following structures:
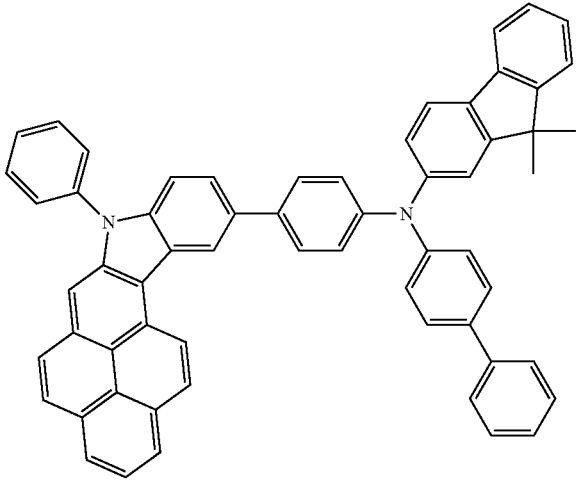
20
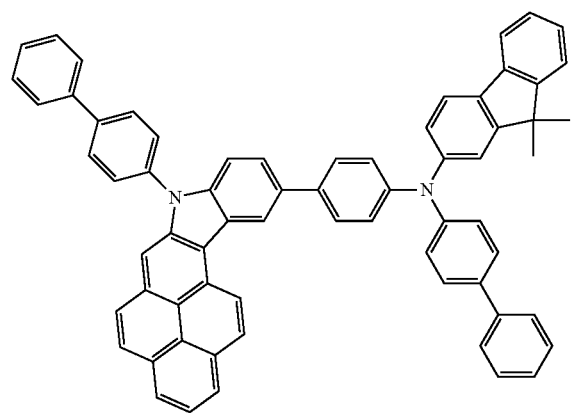
29
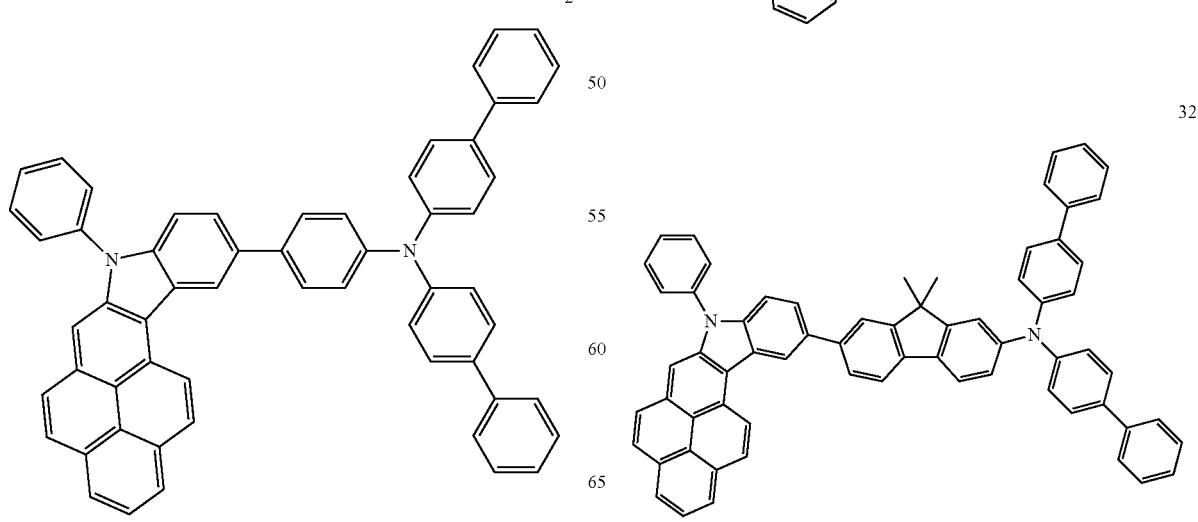
2
32

-continued

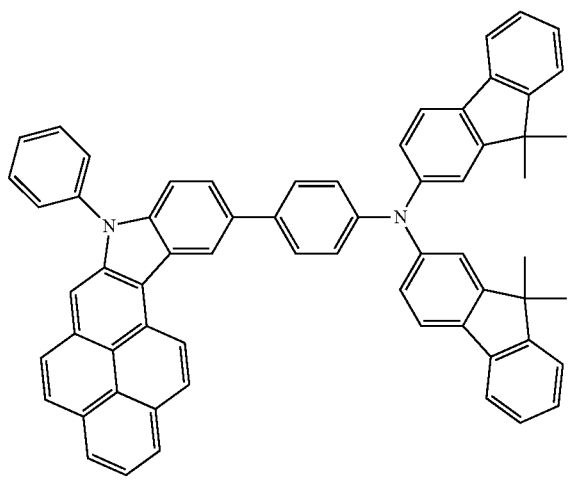

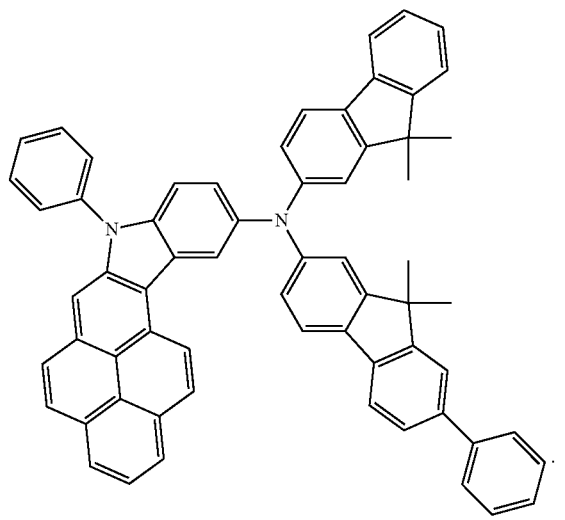

14. An organic light-emitting device comprising:
a first electrode;
a second electrode; and
an organic layer interposed between the first electrode and the second electrode,
wherein the organic layer comprises the amine compound represented by Formula 1 of claim 1.

15. The organic light-emitting device of claim 14, wherein the organic layer is a hole injection layer or a hole transport layer.

16. The organic light-emitting device of claim 14, wherein the organic layer is a single layer having both hole injection and hole transport capabilities.

17. The organic light-emitting device of claim 14, wherein the organic layer is an emission layer, and the amine compound of Formula 1 is used as a host for a fluorescent or phosphorescent device.

18. The organic light-emitting device of claim 14, wherein the organic layer is an emission layer, and the amine compound of Formula 1 is used as a fluorescent dopant.

19. The organic light-emitting device of claim 14, wherein the organic layer comprises an emitting layer, a hole transport layer, and a hole injection layer,
the emitting layer, the hole transport layer, or the hole injection layer comprises the amine compound of Formula 1, and
the emitting layer comprises an anthracene compound, an arylamine compound, or a styryl compound.

20. The organic light-emitting device of claim 14, wherein the organic layer comprises an emitting layer, a hole transport layer, and a hole injection layer,
the emitting layer, the hole transport layer, or the hole injection layer comprises the amine compound of Formula 1, and
one layer selected from the group consisting of a red emitting layer, a green emitting layer, a blue emitting layer, and a white emission layer comprises a phosphorescent compound.

21. The organic light-emitting device of claim 14, wherein the organic layer is formed using a wet process.

22. A flat panel display device comprising the organic light-emitting device of claim 14 and the first electrode of the organic light-emitting device is electrically connected to a source electrode or a drain electrode of a thin film transistor.

* * * * *